(12) United States Patent
Kapeller-Libermann et al.

(10) Patent No.: US 6,369,210 B1
(45) Date of Patent: Apr. 9, 2002

(54) 22012, HUMAN CARBOXYPEPTIDASE

(75) Inventors: Rosana Kapeller-Libermann, Chestnut Hill; Kyle J. MacBeth, Boston; Mark Williamson, Saugus, all of MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/345,469

(22) Filed: Jun. 30, 1999

(51) Int. Cl.$^7$ .......................... C07H 21/04; C07H 5/04; C07H 19/00; C07H 21/00
(52) U.S. Cl. .................. 536/23.5; 435/69.1; 530/350; 536/1; 536/18.7; 536/22.1; 536/23.1; 536/23.2
(58) Field of Search .................. 536/1, 18.7, 22.1, 536/23.1, 23.2, 23.5; 530/350; 435/69.1

(56) References Cited

U.S. PATENT DOCUMENTS 5,808,032 A * 9/1998 Kurihara et al.

FOREIGN PATENT DOCUMENTS

| EP | 0 464 533 A1 | 1/1992 |
| WO | WO 99/18211 | 4/1999 |
| WO | WO 99/66041 | 12/1999 |
| WO | WO 00/42201 | 7/2000 |

OTHER PUBLICATIONS

Amino acid and nucleic acid database, Accession #AA418493, 1997.*
Amino acid and nucleic acid database, Accession #AA303148, 1997.*
Adams et al. Rapid cDNA sequencing (expressed sequence tags) from a directionally cloned human infant brain cDNA library. Nature Genetics 4:373–380, 1993.*
Nucleic acid database, Accession #U62966, 1997.*
Ritzel et al. Molecular cloning and functional expreession of cDNAs encoding a human Na+–nucleoside cotransporter (hCNT1). American Physiological Society:C707–C714, 1997.*
Ausubel et al. Expression of Proteins In *Escherichia cole*. Short Protocols in Molecular Biology. Second edition, Section I. pp. 16–4 to 16–9, 1992.*
Amino acid and Nucleic acid database, Accession #A47352, 1994.*
Amino acid and nucleic acid database, Accession #P42785, 1995.*
Short Protocols in Molecular biology, second edition. Unit 16.1 and 16.2. pp. 16–4 to 16–9, 1992.*
Hillier et al., "The WashU–Merck EST Project," EMBL Database Accession No. N31120, Sequence ID HS120269, Jan. 12, 1996.
National Cancer Institute, "Cancer Genome Anatomy Project (CGAP)," EMBL Database Accession No. A1678665, Sequence ID A1678665, May 27, 1999.
Underwood et al., "Sequence, Purification, and Cloning of an Intracellular Serine Protease, Quiescent Cell Proline of Dipeptidase," *Journal of Biological Chemistry*, Nov. 26, 1999, pp. 34053–34058, vol. 274, No. 8.
Blast Search vs. Patent, NRP, DBEST, and NRN Databases.
Tan et al. (1993), "Sequencing and Cloning of Human Prolylcarboxypeptidase (Angiotensinase C), " *Journal of Biological Chemistry* 268(22):16631–16638.

* cited by examiner

*Primary Examiner*—Anthony C. Caputa
*Assistant Examiner*—Alana M. Harris
(74) *Attorney, Agent, or Firm*—Alston & Bird LLP

(57) ABSTRACT

The present invention relates to a newly identified human carboxypeptidase. The invention also relates to polynucleotides encoding the carboxypeptidase. The invention further relates to methods using the carboxypeptidase polypeptides and polynucleotides as a target for diagnosis and treatment in carboxypeptidase-related disorders. The invention further relates to drug-screening methods using the carboxypeptidase polypeptides and polynucleotides to identify agonists and antagonists for diagnosis and treatment. The invention further encompasses agonists and antagonists based on the carboxypeptidase polypeptides and polynucleotides. The invention further relates to procedures for producing the carboxypeptidase polypeptides and polynucleotides.

5 Claims, 10 Drawing Sheets

```
    CGTCCGGCGGAAGGCGACATGGGCTCCGCTCCCTGGGCCCCGGTCCTGCTGCTGGCGCTC
  1 ---------+---------+---------+---------+---------+---------+ 60
                      M  G  S  A  P  W  A  P  V  L  L  L  A  L   -

GGGCTGCGCGGCCTCCAGGCGGGGGCCCGCAGGGCCCCGGACCCCGGCTTCCAGGAGCGC
 61 ---------+---------+---------+---------+---------+---------+ 120
     G  L  R  G  L  Q  A  G  A  R  R  A  P  D  P  G  F  Q  E  R   -

TTCTTCCAGCAGCGTCTGGACCACTTCAACTTCGAGCGCTTCGGCAACAAGACCTTCCCT
121 ---------+---------+---------+---------+---------+---------+ 180
     F  F  Q  Q  R  L  D  H  F  N  F  E  R  F  G  N  K  T  F  P   -

CAGCGCTTCCTGGTGTCGGACAGGTTCTGGGTCCGGGGCGAGGGGCCCATCTTCTTCTAC
181 ---------+---------+---------+---------+---------+---------+ 240
     Q  R  F  L  V  S  D  R  F  W  V  R  G  E  G  P  I  F  F  Y   -

ACTGGGAACGAGGGCGACGTGTGGGCCTTCGCCAACAACTCGGGCTTCGTCGCGGAGCTG
241 ---------+---------+---------+---------+---------+---------+ 300
     T  G  N  E  G  D  V  W  A  F  A  N  N  S  G  F  V  A  E  L   -

GCGGCCGAGCGGGGGGGCTCTACTGGTCTTCGCGGAGCACCGCTACTACGGGAAGTCGCTG
301 ---------+---------+---------+---------+---------+---------+ 360
     A  A  E  R  G  A  L  L  V  F  A  E  H  R  Y  Y  G  K  S  L   -

CCGTTCGGTGCGCAGTCCACGCAGCGCGGGCACACGGAGCTGCTGACGGTGGAGCAGGCC
361 ---------+---------+---------+---------+---------+---------+ 420
     P  F  G  A  Q  S  T  Q  R  G  H  T  E  L  L  T  V  E  Q  A   -

CTGGCCGACTTCGCAGAGCTGCTCCGCGCGCTACGACGCGACCTCGGGGCCCAGGATGCC
421 ---------+---------+---------+---------+---------+---------+ 480
     L  A  D  F  A  E  L  L  R  A  L  R  R  D  L  G  A  Q  D  A   -

CCCGCCATCGCCTTCGGTGGAAGTTATGGGGGGATGCTCAGTGCCTACCTGAGGATGAAG
481 ---------+---------+---------+---------+---------+---------+ 540
     P  A  I  A  F  G  G  S  Y  G  G  M  L  S  A  Y  L  R  M  K   -

TATCCCCACCTGGTGGCGGGGGCGCTGGCGGCCAGCGCGCCCGTTCTAGCTGTGGCAGGC
541 ---------+---------+---------+---------+---------+---------+ 600
     Y  P  H  L  V  A  G  A  L  A  A  S  A  P  V  L  A  V  A  G   -

CTCGGCGACTCCAACCAGTTCTTCCGGGACGTCACGGCGGACTTTGAGGGCCAGAGTCCC
601 ---------+---------+---------+---------+---------+---------+ 660
     L  G  D  S  N  Q  F  F  R  D  V  T  A  D  F  E  G  Q  S  P   -

AAATGCACCCAGGGTGTGCGGGAAGCGTTCCGACAGATCAAGGACTTGTTCCTACAGGGA
661 ---------+---------+---------+---------+---------+---------+ 720
     K  C  T  Q  G  V  R  E  A  F  R  Q  I  K  D  L  F  L  Q  G   -
```

FIG. 1A.

```
       GCCTACGACACGGTCCGCTGGGAGTTCGGCACCTGCCAGCCGCTGTCAGACGAGAAGGAC
721    ---------+---------+---------+---------+---------+---------+ 780
       A  Y  D  T  V  R  W  E  F  G  T  C  Q  P  L  S  D  E  K  D   -

CTGACCCAGCTCTTCATGTTCGCCCGGAATGCCTTCACCGTGCTGGCCATGATGGACTAC
781    ---------+---------+---------+---------+---------+---------+ 840
       L  T  Q  L  F  M  F  A  R  N  A  F  T  V  L  A  M  M  D  Y   -

CCCTACCCCACTGACTTCCTGGGTCCCCTCCCTGCCAACCCCGTCAAGGTGGGCTGTGAT
841    ---------+---------+---------+---------+---------+---------+ 900
       P  Y  P  T  D  F  L  G  P  L  P  A  N  P  V  K  V  G  C  D   -

CGGCTGCTGAGTGAGGCCCAGAGGATCACGGGGCTGCGAGCACTGGCAGGGCTGGTCTAC
901    ---------+---------+---------+---------+---------+---------+ 960
       R  L  L  S  E  A  Q  R  I  T  G  L  R  A  L  A  G  L  V  Y   -

AACGCCTCGGGCTCCGAGCACTGCTACGACATCTACCGGCTCTACCACAGCTGTGCTGAC
961    ---------+---------+---------+---------+---------+---------+ 1020
       N  A  S  G  S  E  H  C  Y  D  I  Y  R  L  Y  H  S  C  A  D   -

CCCACTGGCTGCGGCACCGGCCCCGACGCCAGGGCCTGGGACTACCAGGCCTGCACCGAG
1021   ---------+---------+---------+---------+---------+---------+ 1080
       P  T  G  C  G  T  G  P  D  A  R  A  W  D  Y  Q  A  C  T  E   -

ATCAACCTGACCTTCGCCAGCAACAATGTGACCGATATGTTCCCCGACCTGCCCTTCACT
1081   ---------+---------+---------+---------+---------+---------+ 1140
       I  N  L  T  F  A  S  N  N  V  T  D  M  F  P  D  L  P  F  T   -

GACGAGCTCCGCCAGCGGTACTGCCTGGACACCTGGGGCGTGTGGCCCCGGCCCGACTGG
1141   ---------+---------+---------+---------+---------+---------+ 1200
       D  E  L  R  Q  R  Y  C  L  D  T  W  G  V  W  P  R  P  D  W   -

CTGCTGACCAGCTTCTGGGGGGGTGATCTCAGAGCCGCCAGCAACATCATCTTCTCCAAC
1201   ---------+---------+---------+---------+---------+---------+ 1260
       L  L  T  S  F  W  G  G  D  L  R  A  A  S  N  I  I  F  S  N   -

GGGAACCTGGACCCCTGGGCAGGGGGCGGGATTCGGAGGAACCTGAGTGCCCTCAGTCATC
1261   ---------+---------+---------+---------+---------+---------+ 1320
       G  N  L  D  P  W  A  G  G  G  I  R  R  N  L  S  A  S  V  I   -

GCCGTCACCATCCAGGGGGGAGCGCACCACCTCGACCTCAGAGCCTCCCACCCAGAAGAT
1321   ---------+---------+---------+---------+---------+---------+ 1380
       A  V  T  I  Q  G  G  A  H  H  L  D  L  R  A  S  H  P  E  D   -

CCTGCTTCCGTGGTTGAGGCGCGGAAGCTGGAGGCCACCATCATCGGCGAGTGGGTAAAG
1381   ---------+---------+---------+---------+---------+---------+ 1440
       P  A  S  V  V  E  A  R  K  L  E  A  T  I  I  G  E  W  V  K   -

GCAGCCAGGCGTGAGCAGCAGCCAGCTCTGCGTGGGGGGCCCAGACTCAGCCTCTGAGCA
1441   ---------+---------+---------+---------+---------+---------+ 1500
       A  A  R  R  E  Q  Q  P  A  L  R  G  G  P  R  L  S  L        -

CAGGACTGGAGGGGTCTCAAGGCTCCTCATGGAGTGGGGGCTTCACTCAAGCAGCTGGCG
1501   ---------+---------+---------+---------+---------+---------+ 1560
```

FIG. 1B.

```
     GCAGAGGGAAGGGGCTGAATAAACGCCTGGAGGCCTGGCAAAAAAAAAAAAAAAAAAAAAA
1561 ---------+---------+---------+---------+---------+---------+ 1620

AAAAAAAAAAAAAAAAAAAAAAAAAAAAAAAAA
1621 ---------+---------+---------+--- 1653
```

FIG. 1C.

```
-----------------------------------------------------------------
Query: 22012
Scores for sequence family classification (score includes all domains):
Model       Description                                 Score    E-value  N
--------    -----------                                 -----    -------  -
abhydrolase alpha/beta hydrolase fold                   31.8     1.6e-05  1
Peptidase_S9 Prolyl oligopeptidase family                8.4      0.25    1
Parsed for domains:
Model        Domain  seq-f  seq-t    hmm-f  hmm-t     score   E-value
------       ------  -----  -----    -----  -----     -----   -------
Peptidase_S9  1/1     158    167 ..    72     81 .)    8.4     0.25
abhydrolase   1/1     100    360 ..     1    233 ()   31.8    1.6e-05

Alignments of top-scoring domains:
Peptidase_S9: domain 1 of 1, from 158 to 167: score 8.4, E = 0.25
                   *->ifGgSnGGiL<-*
                      +fGgS+GG+L
         22012  158   AFGGSYGGML     167 abhydrolase: domain 1 of 1, from 100 to 360: score 31.8, E = 1.6e-05
                   *->frvialDlrGfGeSsrp............sdladyrfddlaedleal
                      +  ++  + +r++G+S  p + ++++++++++ + +   +d+ae  l al
         22012  100   ALLVFAEHRYYGKSL-PfgaqstqrghteLLTVEQALADFAELLRAL 145 ldalgldkp.vilvGhSmGGalaaayaakyPeervkalvlvstp....ap
                      ++ lg +   ++i++G+S+GG+l+a++++kyP+ +v+++ + s+p     a
         22012  146   RRDLGAQDApAIAFGGSYGGMLSAYLRMKYPH-LVAGALAASAPvlavAG 194 aglssrlfprlgnleglllanffnrlsrsveallgralkqffllgrpfvs
                      g s+ +f++ ++ ++ ++ ++++    +ea++++ + +fl g +
         22012  195   LGDSNQFFRDVTADFEGQSPKCTQ---GVREAFRQIKD--LFLQGAY--- 236 dflkqaedwlssslarp.getdggdgllgy...avalgkllqwdrs.alkd
                      d +++++++++ l++++  t+ ++   ++ + + + + +d+ ++l+
         22012  237   DTVRWEFGTCQPLSDEkDLTQLFMFARNAftvLAMMDYPYPTDFLgPLPA 286

..ikvPtlviwgddDplvplkaseklsalfpna.evvviddagHla....
                      +++kv  +  +  +++ l a   l + ++++ +++i  +H  +++
         22012  287   npVKVGCDRLLSEAQRITGLRALAGLVYNASGSeHCYDIYRLYHSCadpt 336

........llekpeevaeli.kfl<-*
                      +  +++++   +++++++e+    f+
         22012  337   gcgtgpdaRAWDYQACTEINlTFA     360
```

FIG. 2.

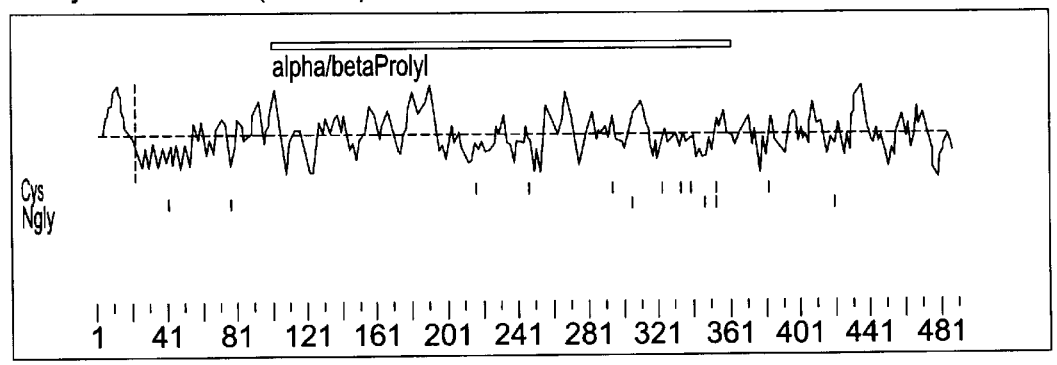

Analysis of 22012 (492 aa)

>22012
MGSAPWAPVLLLALGLRGLQAGARRAPDPGFQERFFQQRLDHFNFERFGNKTFPQRFLVS
DRFWVRGEGPIFFYTGNEGDVWAFANNSGFVAELAAERGALLVFAEHRYYGKSLPFGAQS
TQRGHTELLTVEQALADFAELLRALRRDLGAQDAPAIAFGGSYGGMLSAYLRMKYPHLVA
GALAASAPVLAVAGLGDSNQFFRDVTADFEGQSPKCTQGVREAFRQIKDLFLQGAYDTVR
WEFGTCQPLSDEKDLTQLFMFARNAFTVLAMMDYPYPTDFLGPLPANPVKVGCDRLLSEA
QRITGLRALAGLVYNASGSEHCYDIYRLYHSCADPTGCGTGPDARAWDYQACTEINLTFA
SNNVTDMFPDLPFTDELRQRYCLDTWGVWPRPDWLLTSFWGGDLRAASNIIFSNGNLDPW
AGGGIRRNLSASVIAVTIQGGAHHLDLRASHPEDPASVVEARKLEATIIGEWVKAARREQ
QPALRGGPRLSL

FIG. 4.

Prosite Pattern Matches for 22012
Prosite version: Release 12.2 of February 1995

>PS00001/PDOC00001/ASN_GLYCOSYLATION N-glycosylation site.

| | | | |
|---|---|---|---|
| Query: | 50 | NKTF | 53 |
| Query: | 86 | NNSG | 89 |
| Query: | 315 | NASG | 318 |
| Query: | 356 | NLTF | 359 |
| Query: | 363 | NVTD | 366 |
| Query: | 428 | NLSA | 431 |

>PS00005/PDOC00005/PKC_PHOSPHO_SITE Protein kinase C phosphorylation site.

| | | | |
|---|---|---|---|
| Query: | 60 | SDR | 62 |
| Query: | 121 | TQR | 123 |
| Query: | 213 | SPK | 215 |
| Query: | 238 | TVR | 240 |

>PS00006/PDOC00006/CK2_PHOSPHO_SITE Casein kinase II phosphorylation site.

| | | | |
|---|---|---|---|
| Query: | 75 | TGNE | 78 |
| Query: | 317 | SGSE | 320 |
| Query: | 331 | SCAD | 334 |
| Query: | 340 | TGPD | 343 |
| Query: | 450 | SHPE | 453 |
| Query: | 457 | SVVE | 460 |

>PS00008/PDOC0008/MYRISTYL N_myristoylation site.

| | | | |
|---|---|---|---|
| Query: | 18 | GLQAGA | 23 |
| Query: | 117 | GAQSTQ | 122 |
| Query: | 160 | GGSYGG | 165 |
| Query: | 181 | GALAAS | 186 |
| Query: | 194 | GLGDSN | 199 |
| Query: | 219 | GVREAF | 224 |
| Query: | 234 | GAYDTV | 239 |
| Query: | 311 | GLVYNA | 316 |
| Query: | 318 | GSEHCY | 323 |
| Query: | 424 | GIRRNL | 429 |

>PS00029/PDOC00029/LEUCINE_ZIPPER Leucine zipper pattern.

| | | | |
|---|---|---|---|
| Query: | 128 | LLTVEQALADFAELLRALRRDL | 149 |

FIG. 5.

22012, HUMAN CARBOXYPEPTIDASE

FIELD OF THE INVENTION

The present invention relates to a newly identified human carboxypeptidase. The invention also relates to polynucleotides encoding the carboxypeptidase. The invention further relates to methods using the carboxypeptidase polypeptides and polynucleotides as a target for diagnosis and treatment in carboxypeptidase-related disorders. The invention further relates to drug-screening methods using the carboxypeptidase polypeptides and polynucleotides to identify agonists and antagonists for diagnosis and treatment. The invention further encompasses agonists and antagonists based on the carboxypeptidase polypeptides and polynucleotides. The invention further relates to procedures for producing the carboxypeptidase polypeptides and polynucleotides.

BACKGROUND OF THE INVENTION

Proteolytic enzymes are involved in many cellular processes. The carboxypeptidase family of enzymes catalyze, the cleavage of C-terminal amino acids of peptides and proteins, altering their biological activity. Lysosomal carboxypeptidase enzymes are highly concentrated in lysosomes, but may also be active extracellularly after their release from lysosomes in soluble form or bound to transmembrane or other membrane-associated proteins. Carboxypeptidases may cleave peptides in a sequence-specific manner. For example, prolylcarboxypeptidases cleave only peptides linked to proline residues (for example, des-Arg9-bradykinin, angiotensin II). There is also evidence that these enzymes are involved in terminating signal transduction by inactivating peptide ligands after receptor endocytosis.

In contrast to endoproteases which cleave internal peptide bonds of proteins and polypeptides, carboxypeptidases (CPs) catalyze the cleavage of only the C-terminal peptide bond, releasing one amino acid at a time. The two main groups of CPs include serine CPs and metallo-CPs, the serine CPs containing a signature trio of Ser, Asp, His in the active site. This trio is also contained in prolylendopeptidase serine proteases. Serine CPs include polycarboxypeptidase (PRCP) also referred to as angiotensinase C; and deamidase, also referred to as cathepsin A and lysosomal protective protein. See Skidgel et al. (1998) *Immunological Reviews* 161:129–141.

Metallo-CPs contain a signature glutamic acid as the primary catalytic residue and require zinc-binding for activity. Metallo-CPs can be grouped by substrate specificity into CPA and CPB types; the CPA type preferentially cleaving C-terminal hydrophobic residues, and the CPB type cleaving only peptides with C-terminal basic Arg or Lys residues. See R. A. Skidgel (1993) In: Hooper N M, ed. *Zinc Metalloproteases in Health and Disease*, London: Taylor & Francis, Ltd., p. 241–283.

CPM is a B type carboxypeptidase which is anchored on cell membranes via gylcosylphosphatidylinositol (GPI) association with its mildly hydrophobic stretch of 15 C-terminal amino acids. As in many other proteins sharing this anchoring mechanism, CPM is released from the membrane by bacterial phosphatidylinositol-specific phospholipase C. Human CPM is a glycoprotein of 426 amino acid residues with 43% identity to human intracellular secretory granular CP (CPE), 41% with the active 50 kDa subunit of human plasma CPN, and 15% with bovine pancreatic CPA or CPB. The active sites of these CPs contain conserved amino acid residues corresponding to the zinc binding residues $His^{66}Glu^{69}$ and $His^{173}$, substrate binding residues $Arg^{137}$ and $Tyr^{242}$, and the catalytic $Glu^{264}$, as designated for CPM. Sequence homologies around these conserved residues is high, with an identity between CPs M, E and N of approximately 70–90%. See Tan et al. (1989) *J. Biol. Chem.* 264:13165–13170; Deddish et al. (1990) *J. Biol. Chem.* 265:15083–15089; R. A. Skidgel (1993) In: Hooper N M, ed. *Zinc Metalloproteases in Health and Disease*, London: Taylor & Francis, Ltd., p. 241–283. CPM has been mapped to the chromosomal location of chromosome 12q13-q15 which is associated with a variety of solid tumors.

The optimal pH range of CPM is in the neutral range of 6.5–7.5. As no endogenous inhibitors are known for CPM, the enzyme is considered to be constitutively active. Synthetic inhibitors including Arg analogs DL-2mercaptomethyl-3-guanidinoethylthiopropanoic acid (MGTA) and guanidinoethylmercaptosuccinic acid (GEMSA) inhibit CPM. See R. A. Skidgel (1991) In: Conn P M, ed. *Methods in Neurosciences: Peptide Technology* Vol. 6, Orlando: Academic Press, p. 373–385; Plummer et al. (1981) *Biochem. Biophys. Res. Comm.* 98: 448–254.

As with other B type regulatory CPs, CPM cleaves only C-terminal Arg or Lys residues; however, CPM has a preference for the C-terminal Arg. The penultimate amino acid also affects the rate of hydrolysis. Naturally occurring peptide substrates of CPM include bradykinin, $Arg^6$- and $Lys^6$ enkephalins, dynorphin $A^{1-13}$ and epidermal growth factor (EGF). See Sidgel et al. (1989) *J. Biol. Chem.* 264:2236–2241; McGwire et al. (1995) *J. Biol. Chem.* 270:17154–17158.

CPM is primarily found on the plasma membrane, with highest levels found in lung and placenta. It is also present in kidney, blood vessels, intestine, brain and peripheral nerves. See R. A. Skidgel (1988) *Trends Pharm. Sci.* 9:299–304; Skidgel et al. (1984) *Biochem. Pharmacol.* 33: 3471–3478; Skidgel et al. (1991) *FASEB J.* 5: 1578; Nagae et al. (1992) *J. Neurochem.* 59:2201–2212; Nagae et al. (1993) *Am. J. Respir. Cell Mol. Biol.* 9:221–229. Expression of CPM is responsive to differentiation of monocytes and lymphocytes. See de Saint-Vis et al. (1995) *Blood* 86:1098–1105; Rehli et al. (1995) *J. Biol. Chem.* 270:15644–15649.

CPM participates in the control of peptide hormone activity at the cell surface and degradation of extracellular proteins and peptides. It catalyzes the second step in prohormone processing and removes C-terminal Arg or Lys residues from peptides released from prohormones. CPM functions as a soluble enzyme after its release from the plasma membrane and may function in the plasma membrane form to control peptide receptor activities. CPM can regulate receptor specificity of kinins by cleaving the C-terminal $ARG^9$, for example, from bradykinin. The intact bradykinin binds the B2 receptor. The cleaved bradykinin (des-$ARG^9$-bradykinin). Des-$ARG^9$-bradykinin also binds the B1 receptors: stimulates IL-1 and tumor necrosis factor release from macrophages. Regulation of the B1 receptor is associated with injury or inflammation. CPM may also be involved with other inflammatory mediators, such as anaphylatoxin C5a which mediates histamine release. In addition, CPM may metabolize growth factors containing terminal Arg or Lys, such as EGF, EGF-like peptides, nerve growth factor (NGF) amphiregulin, hepatocyte growth factor, erythropoietin, and macrophage-stimulating protein. In the lung, varying levels of CPM are associated with pneumocystic or bacterial pneumonia or lung cancer, and in the placenta, CPM may protect the fetus from maternally derived peptides. See R. A. Skidgel (1992) *J. Cardiovasc. Pharmacol.* 20(Suppl. 9):S4–S9; Bhoola et al. (1992) *Phar-* macol. Rev. 44:1–80; R. A. Skidgel (1993) In: Hooper N M, ed. *Zinc Metalloproteases in Health and Disease*, London: Taylor & Francis, Ltd., p. 241–283; Dragovic et al. (1995) *Am. J. Respir. Crit. Care Med.* 152:760–764; Nagae et al. (1992) *J. Neurochem.* 59:2201–2212; MacFadden et al. (1988) *FASEB J.* 2:1179 (Abstract).

Another B-type regulatory CP metalloprotein is CPD, a membrane-bound glycoprotein. Human CPD is a protein of 1,377 amino acids with 75% identity with duck GP180 and 90% identity with rat CPD. Human CPD contains two hydrophobic regions located at the C- and N-termini. A 55–60 residue cytoplasmic domain is highly conserved among duck, human and rat sequences and may be significant in intracellular sorting, protein-protein interactions or endocytosis. CPD contains three tandem CP homology domains numbered sequentially from the N- to the C-terminus, and thereby may contain more than one active site. See Tan et al. (1997) *Biochem. J.* 327:81–87; Skidgel et al. (1993) In: Robertson J L S, Nicholls M G, eds. *The Renin Angiotensin System*, Vol. 1, London: Gower Medical Publishing, p. 10.1–10.10. CPD is located on human chromosome 17, 17P, 11.1–17q, 11.2.

CPD is primarily found on intracellular membranes, mainly in the Golgi, with some CPD found on the plasma membrane. The tissue distribution of CPD is wide and includes most duck tissues and mammalian tissues as well, including brain, pituitary, placenta, pancreas, adrenal, kidney, lung, heart, spleen, intestine, ovary, and testes. See McGwire et al. (1997) *Life Sci.* 60:715–724; Song et al. (1995) *J. Biol. Chem.* 270:25007–25013; Xin et al. (1997) *DNA Cell Biol.* 16:897–909; Tan et al. (1997) *Biochem. J.* 327:81–87; Song et al. (1996) *J. Biol. Chem.* 271:28884–28889.

The function of CPD is speculated to include peptide and protein processing in the constitutive secretory pathway after endoprotease cleavage of precursor proteins. The enzyme has an acidic pH optimum. Mammalian CPD may act as a hepatitis B virus binding protein, similar to the duck CPD. See R. A. Skidgel (1998) *Immunological Reviews* 161:129–141.

Serine CPs include PRCP and deamidase. PRCP cloned from a human kidney library indicates a glycoprotein of 51kDa$^3$; and containing 496 amino acids, including a 30 residue signal peptide and a 15 residue propeptide. See Tan et al. (1993) *J. Biol. Chem.* 268:16631–16638. A serine repeat is found in the C-terminal half, similar to the serine repeat of a yeast CP encoded by the KEX1 gene.

PRCP has an acidic pH optimum for synthetic peptide substrates, but retains activity at neutral ranges with longer naturally occurring peptides. PRCP cleaves peptides only if the penultimate residue is proline. The enzyme does not cleave Pro-Pro-COOH or (OH)-Pro-Pro-COOH bond. See Odya et al. (1978) *J. Biol. Chem.* 253:5927–5931. Substrates of PRCP include des-Arg$^9$-bradykinin and angiotensin II.

PRCP may be involved in terminating signal transduction by inactivating peptide ligands after receptor endocytosis. PRCP is contained in lysosomes and released in response to stimulation. The enzyme is widely distributed and found in human placenta, lung, liver, and kidney.

Another serine CP, deamidase, is likely a 94 kDa homodimer of 52 kDa subunits. Human platelet deamidase is activated by cleavage of a 14 amino acid fragment from the C-terminus. The enzyme binds and maintains activity and stability of -galactocidase and neuraminidase in lysosomes, a defect of which is associated with severe galactosialidosis. See Bonten et al. (1995) *J. Biol. Chem.* 270:26441–26445; Galjart et al. (1988) *Cell* 54:755–764; D'Azzo et al. (1982) *Proc. Natl. Acad. Sci.* 79:4535–4539. The gene for the human deamidase is mapped to chromosome 20 at q13.1.

Deamidase cleaves various peptides containing C-terminal or penultimate hydrophobic residues including substance P, angiotensin I, bradykinin, endothelin, and fMet-Leu-Phe. Like PRCP, deamidase is also found in lysosomes, and distributed in human placenta, lung, liver, and kidney. Like PRCP, deamidase is implicated in blocking part of the signal transduction pathway stimulated by peptides. Bradykinin, containing a C-terminal Arg$^9$ and a penultimate hydrophobic amino acid Phe$^8$, is cleaved by deamidase. Similarly, angiotensin, containing a C-terminal His and a penultimate Phe, is cleaved by deamidase. Accordingly, deamidase is implicated in termination of bradykinin activity on the B2 receptor to generate a B1 receptor agonist. Deamidase may also have a role in chemotaxis and in metabolism of the anti-cancer growth factor antagonist. See Skidgel et al. (1998) *Immunological Reviews* 161:129–141; Jackman et al. (1990) *J Biol. Chem.* 265:11265–11272; Jackman et al. (1995) *Am. J. Respir. Cell Mol. Biol.* 13:196–204; Hinek et al. (1996) *Biol. Chem.* 377:471–480; Jones et al. (1995) *Peptides* 16:777–783; Cummings et al. (1995) *Biochem Pharmacol.* 49:1709–1712.

Given the wide distribution and various physiological and pathological roles of carboxypeptidases, methods and compositions directed at regulating levels of these enzymes are useful for regulating peptide hormone activity, modulating metabolism of substance P, angiotensin I, angiotensin II, bradykinin, and endothelin, and regulation of signal transduction by inactivation of peptide ligands subsequent to receptor endocytosis.

Accordingly, carboxypeptidases are a major target for drug action and development. Therefore, it is valuable to the field of pharmaceuticals development to identify and characterize previously unknown carboxypeptidases. The present invention advances the state of the art by providing a previously unidentified human carboxypeptidase.

SUMMARY OF THE INVENTION

It is an object of the invention to identify novel carboxypeptidases.

It is a further object of the invention to provide novel carboxypeptidase polypeptides that are useful as reagents or targets in carboxypeptidase assays applicable to treatment and diagnosis of carboxypeptidase-related disorders.

It is a further object of the invention to provide polynucleotides corresponding to the novel carboxypeptidase polypeptides that are useful as targets and reagents in carboxypeptidase assays applicable to treatment and diagnosis of carboxypeptidase-related disorders and useful for producing novel carboxypeptidase polypeptides by recombinant methods.

A specific object of the invention is to identify compounds that act as agonists and antagonists and modulate the expression of the novel carboxypeptidase.

A further specific object of the invention is to provide compounds that modulate expression of the carboxypeptidase for treatment and diagnosis of carboxypeptidase-related disorders.

The invention is thus based on the identification of a novel human carboxypeptidase. The amino acid sequence is shown in SEQ ID NO 1. The nucleotide sequence is shown as SEQ ID NO 2.

The invention provides isolated carboxypeptidase polypeptides, including a polypeptide having the amino acid sequence shown in SEQ ID NO 1 or the amino acid sequence encoded by the cDNA deposited as ATCC No. PTA-1643 on Apr. 5, 2000 ("the deposited cDNA").

The invention also provides isolated carboxypeptidase nucleic acid molecules having the sequence shown in SEQ ID NO 2 or in the deposited cDNA.

The invention also provides variant polypeptides having an amino acid sequence that is substantially homologous to the amino acid sequence shown in SEQ ID NO 1 or encoded by the deposited cDNA.

The invention also provides variant nucleic acid sequences that are substantially homologous to the nucleotide sequence shown in SEQ ID NO 2 or in the deposited cDNA.

The invention also provides fragments of the polypeptide shown in SEQ ID NO 1 and nucleotide sequence shown in SEQ ID NO 2, as well as substantially homologous fragments of the polypeptide or nucleic acid.

The invention further provides nucleic acid constructs comprising the nucleic acid molecules described herein. In a preferred embodiment, the nucleic acid molecules of the invention are operatively linked to a regulatory sequence.

The invention also provides vectors and host cells for expressing the carboxypeptidase nucleic acid molecules and polypeptides, and particularly recombinant vectors and host cells.

The invention also provides methods of making the vectors and host cells and methods for using them to produce the carboxypeptidase nucleic acid molecules and polypeptides.

The invention also provides antibodies or antigen-binding fragments thereof that selectively bind the carboxypeptidase polypeptides and fragments.

The invention also provides methods of screening for compounds that modulate expression or activity of the carboxypeptidase polypeptides or nucleic acid (RNA or DNA).

The invention also provides a process for modulating carboxypeptidase polypeptide or nucleic acid expression or activity, especially using the screened compounds. Modulation may be used to treat conditions related to aberrant activity or expression of the carboxypeptidase polypeptides or nucleic acids.

The invention also provides assays for determining the activity of or the presence or absence of the carboxypeptidase polypeptides or nucleic acid molecules in a biological sample, including for disease diagnosis.

The invention also provides assays for determining the presence of a mutation in the polypeptides or nucleic acid molecules, including for disease diagnosis.

In still a further embodiment, the invention provides a computer readable means containing the nucleotide and/or amino acid sequences of the nucleic acids and polypeptides of the invention, respectively.

DESCRIPTION OF THE DRAWINGS

FIG. 1 shows the carboxypeptidase nucleotide sequence (SEQ ID NO 2) and the deduced amino acid sequence (SEQ ID NO 1).

FIG. 2 shows a comparison of the carboxypeptidase against the Prosite database of protein patterns, specifically showing a high score against the prolyloligopeptidase family. (SEQ ID NO: 3) AND AN ALPHA/BETA HYDROLASE (SEQ ID NO: 4)

FIG. 4 shows a hydrophobicity plot of the carboxypeptidase. (SEQ ID NO: 1)

FIG. 5 shows an analysis of the carboxypeptidase open reading frame for amino acids corresponding to specific functional sites. Glycosylation sites, protein kinase C phosphorylation sites, casein kinase II phosphorylation sites, N-myristoylation sites, and leucine zipper pattern are shown. SEQ ID NO: 1

DETAILED DESCRIPTION OF THE INVENTION

Polypeptides

Figure 3:
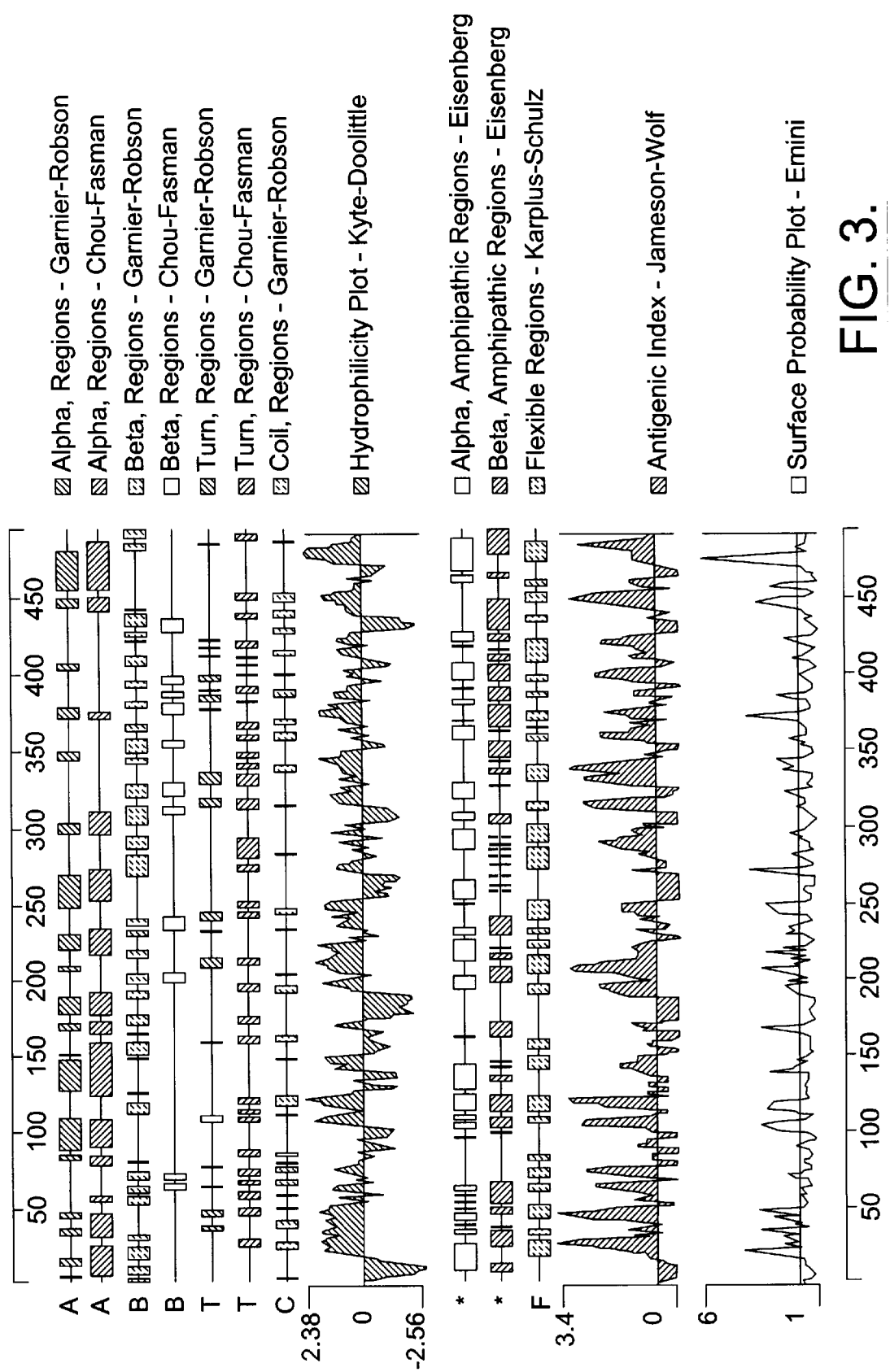
FIG. 3 shows an analysis of the carboxypeptidase amino acid sequence: αβturn and coil regions; hydrophilicity; amphipathic regions; flexible regions; antigenic index; and surface probability plot.
Figure 6:
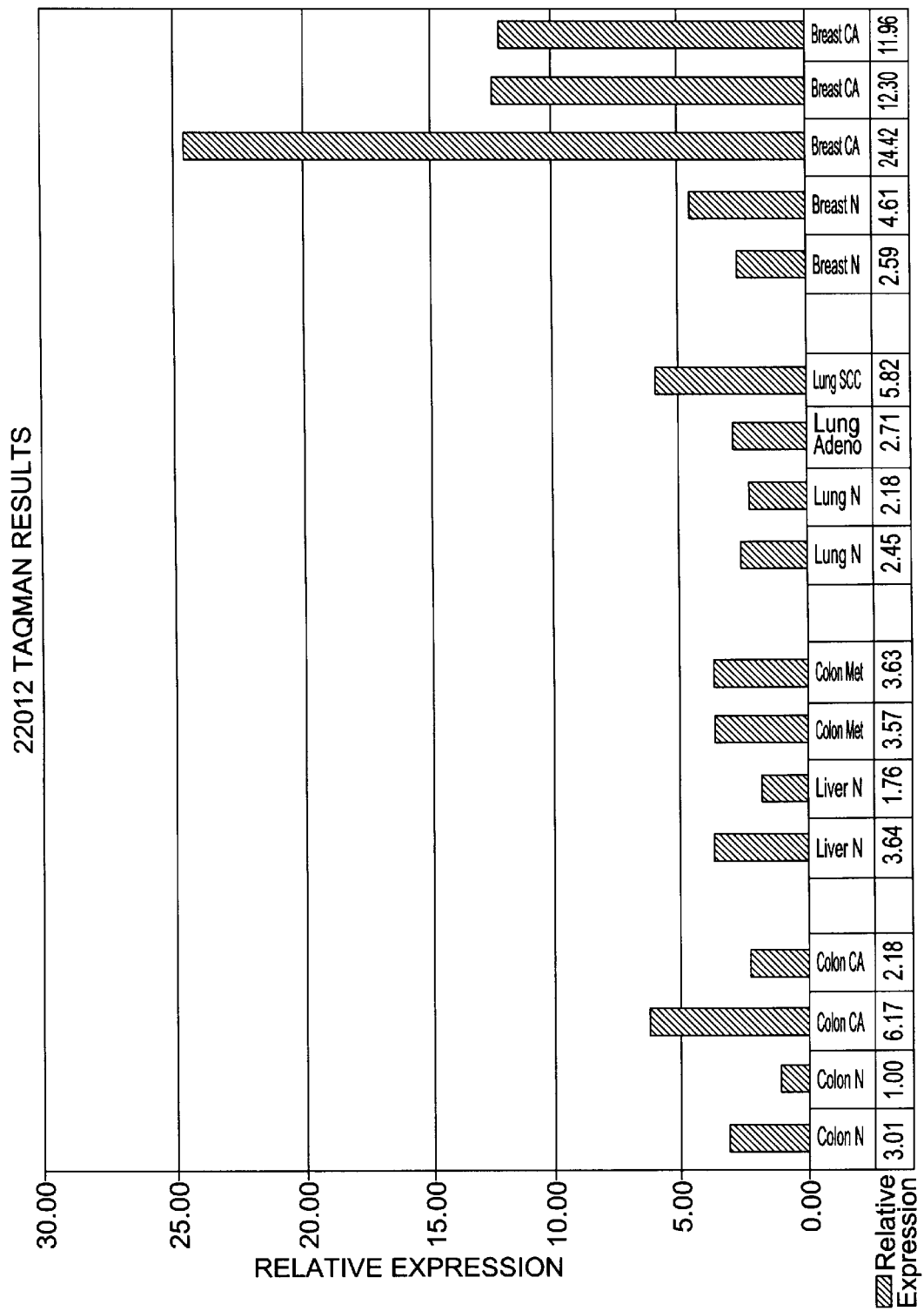
FIG. 6 shows RNA expression of the carboxypeptidase in normal and tumor tissues.
Figure 7:
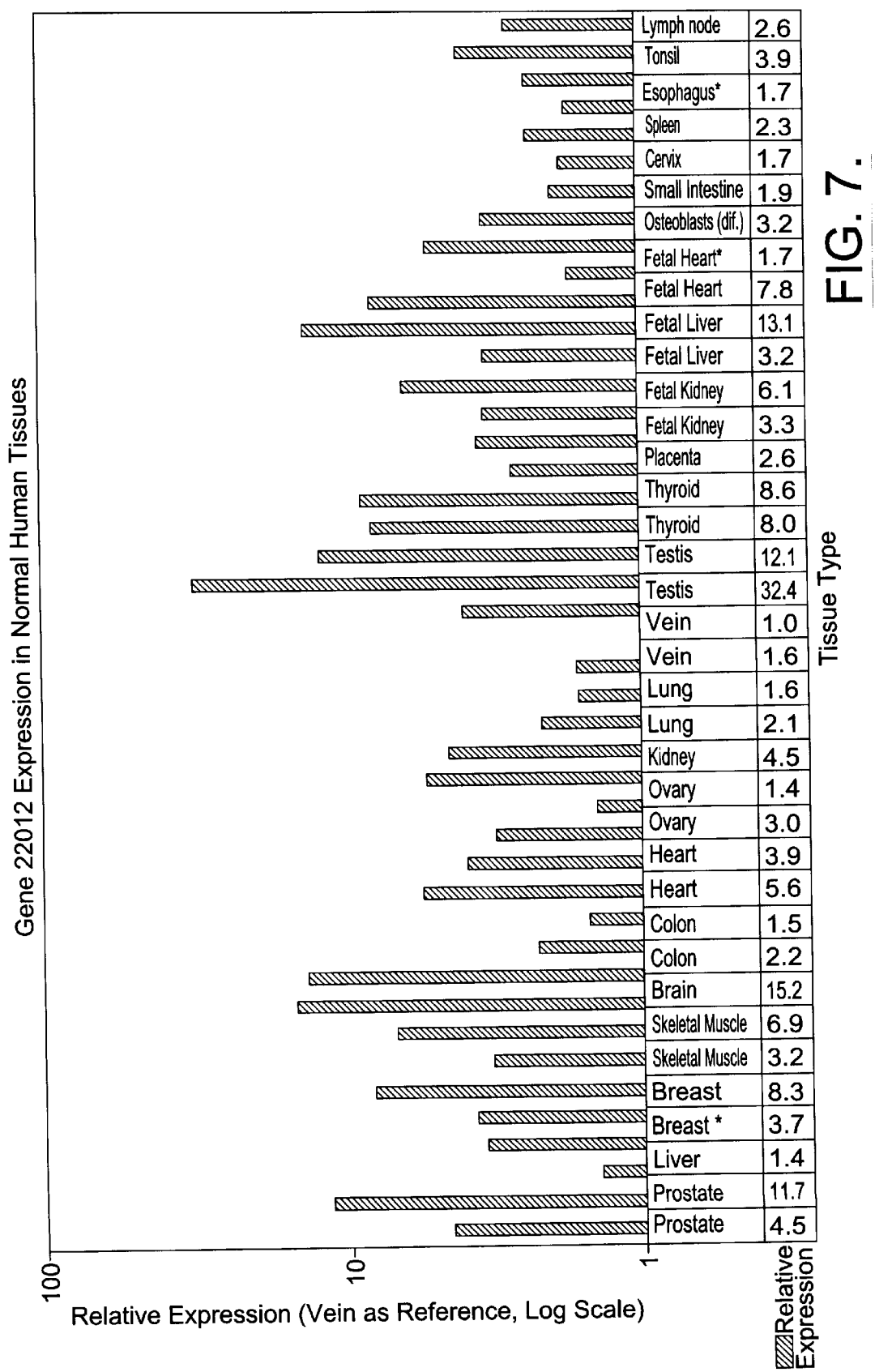
FIG. 7 shows RNA expression of the carboxypeptidase in normal human tissues.
Figure 8:
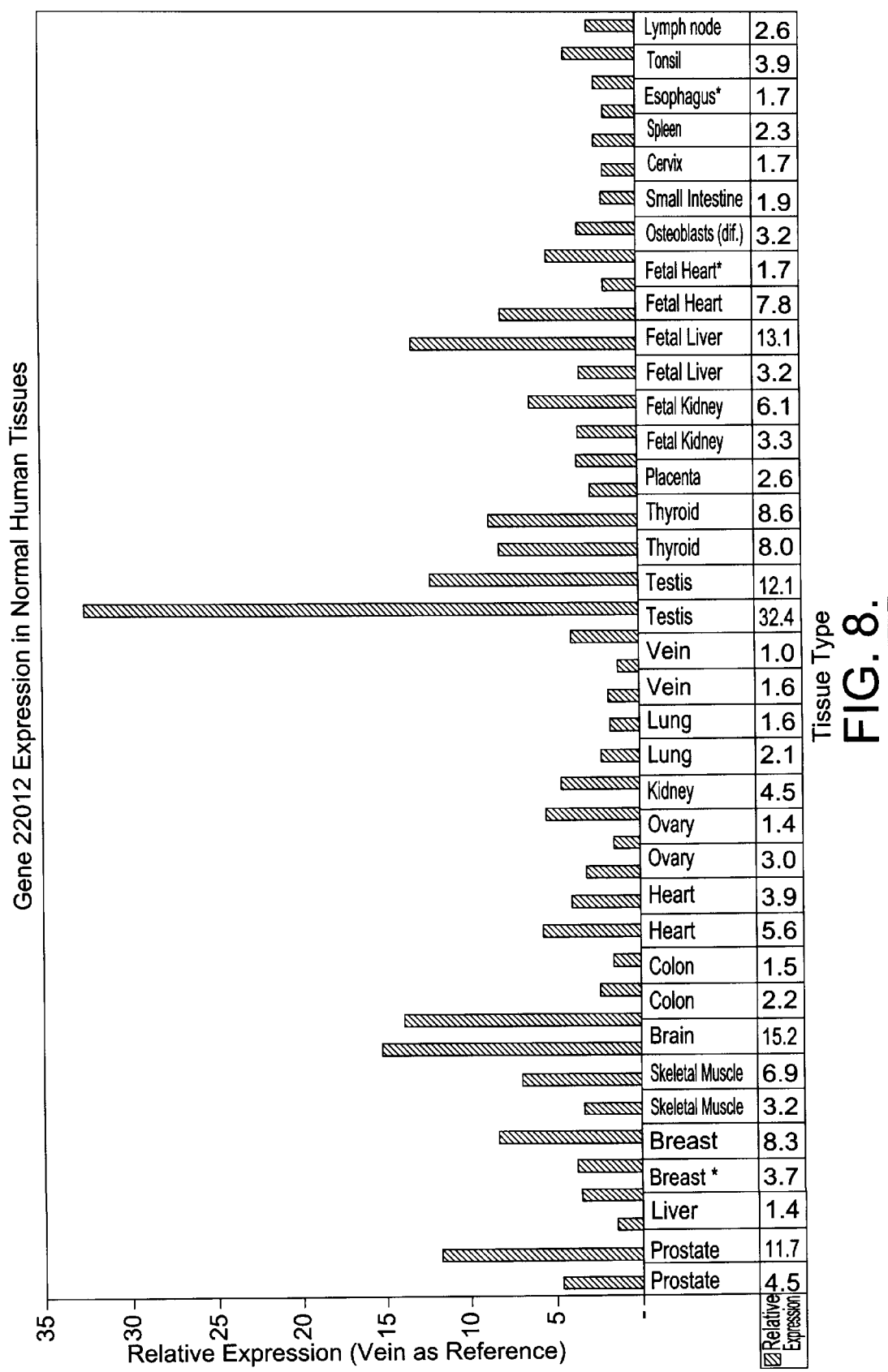
FIG. 8 shows RNA expression of the carboxypeptidase in normal human tissues.

The invention is based on the discovery of a novel human carboxypeptidase. Specifically, an expressed sequence tag (EST) was selected based on homology to carboxypeptidase sequences. This EST was used to design primers based on sequences that it contains and used to identify a cDNA found in osteoblast, brain, small intestine, heart, and prostate cDNA libraries. Positive clones were sequenced and the overlapping fragments were assembled. Analysis of the assembled sequence revealed that the cloned cDNA molecule encodes a carboxypeptidase.

The invention thus relates to a novel carboxypeptidase having the deduced amino acid sequence shown in FIG. 1 (SEQ ID NO 1) or having the amino acid sequence encoded by the deposited cDNA, ATCC No. PTA-1643.

The deposit will be maintained under the terms of the Budapest Treaty on the International Recognition of the Deposit of Microorganisms. The deposit is provided as a convenience to those of skill in the art and is not an admission that a deposit is required under 35 U.S.C. § 112. The deposited sequence, as well as the polypeptide encoded by the sequence, is incorporated herein by reference and controls in the event of any conflict, such as a sequencing error, with description in this application.

The carboxypeptidase of the invention has homology to the family of prolylendopeptidases. The catalytic triad signature, SER ASP HIS, is found in the protein of the invention as well as in prolylcarboxypeptidase (angiotensinase C NOBF [P42785], PCP). PCP is classified as belonging to the prolylendopeptidase and serine carboxypeptidase family. The amino acids around the SER in PCP is consistent with a prolylendopeptidase. The ones found in the polypeptide of the invention are more similar to the ones found in the serine carboxypeptidase family.

"Carboxypeptidase polypeptide" or "carboxypeptidase protein" refers to the polypeptides in SEQ ID NO 1 or encoded by the deposited cDNA. The term "carboxypeptidase protein" or "carboxypeptidase polypeptide", however, further includes the numerous variants described herein, as well as fragments derived from the fill-length carboxypeptidase and variants.

Tissues and/or cells in which the carboxypeptidase is found include, but are not limited to, those found in the figures herein. In particular, the carboxypeptidase is expressed in prostate, breast, skeletal muscle, brain, testis, thyroid, fetal kidney, fetal liver, and fetal heart tissues. Disease expression is associated with colon carcinoma, breast carcinoma, and lung squamous cell carcinoma. Expression has been observed in HCT116, a variant cell line isolated from a colon carcinoma, HT29, an adenocarcinoma line, KM12, a weakly metastatic colorectal carcinoma cell line, and HTC8, a colon carcinoma cell line. Expression has also been observed in the breast carcinoma cell line MDA-231, MCF-7, HMEC, ZR-75, and MDA-435. Up-regulation has been observed in HCT116, DLD-1 (adenocarcinoma of the sigmoid colon), HT29, SW480 (adenocarcinoma from metastatic lymph node), SW620 (adenocarcinoma from metastatic lymph node), and KM12. Thus, this carboxypeptidase is overexpressed in a number of breast, lung and colon tumors, including colon carcinoma, lung adenocarcinoma, small cell lung carcinoma, and colon metastatic tissue. Elevated levels in clinical cancerous tumors and not in noncancerous normal tissues indicate a cellular proteolytic imbalance in these tissues. Accordingly, expression of the carboxypeptidase is relevant to carcinogenesis, including invasion and metastasis.

The present invention thus provides an isolated or purified carboxypeptidase polypeptide and variants and fragments thereof.

Based on a BLAST search, highest homology was shown to a human prolylcarboxypeptidase.

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

The carboxypeptidase polypeptides can be purified to homogeneity. It is understood, however, that preparations in which the polypeptide is not purified to homogeneity are useful and considered to contain an isolated form of the polypeptide. The critical feature is that the preparation allows for the desired function of the polypeptide, even in the presence of considerable amounts of other components. Thus, the invention encompasses various degrees of purity.

In one embodiment, the language "substantially free of cellular material" includes preparations of the carboxypeptidase having less than about 30% (by dry weight) other proteins (i.e., contaminating protein), less than about 20% other proteins, less than about 10% other proteins, or less than about 5% other proteins. When the polypeptide is recombinantly produced, it can also be substantially free of culture medium, i.e., culture medium represents less than about 20%, less than about 10%, or less than about 5% of the volume of the protein preparation.

A carboxypeptidase polypeptide is also considered to be isolated when it is part of a membrane preparation or is purified and then reconstituted with membrane vesicles or liposomes.

The language "substantially free of chemical precursors or other chemicals" includes preparations of the carboxypeptidase polypeptide in which it is separated from chemical precursors or other chemicals that are involved in its synthesis. In one embodiment, the language "substantially free of chemical precursors or other chemicals" includes preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

In one embodiment, the carboxypeptidase polypeptide comprises the amino acid sequence shown in SEQ ID NO 1. However, the invention also encompasses sequence variants. Variants include a substantially homologous protein encoded by the same genetic locus in an organism, i.e., an allelic variant. The carboxypeptidase has been mapped to human chromosome 9 at 9q33–34. Nearby known genes include DYT1, CAIN, VAV2, NOTCH1, ABL1, SDHD, TSC1, SURF1, RPL7A, RXRA, COL5A1, PAEP, ABC2, N14, LCN1, CACNA1B, FCN1. Nearby mutations/loci include Human-DYS, DYSAUTONOMIA, FAMILIAL; MUSCULAR DYSTROPHY, LIMB-GIRDLE, TYPE 2H; AFD1, ACROFACIAL DYSOSTOSIS 1, BDB1, NAGER TYPE; BRACHYDACTYLY, TYPE B1; ALS4, AMYOTROPHIC LATERAL SCLEROSIS 4, JUVENILE.

A possible locus in the mouse is on chromosome 2 and possibly chromosome 4. In the mouse, the Scc2 locus controls susceptibility to 1,2 dimethylhydrazine-induced colon tumors. The following loci in the mouse are relevant: Mouse Chr2- Scc2, colon tumor susceptibility 2; stu, stumbler; Sd, Danforth's short tail; stb, stubby; us, urogenital syndrome; ebo, ebouriffe; sar, sarcosinemia autosomal recessive; Lsr1, listeria resistance; Anth2, resistance to Bacillus anthracis 2; mdm, muscular dystrophy with myositis. See Moen, C. J. et al. *Proc. Natl. Acad. Sci. U.S.A.* 93 (1996).

Variants also encompass proteins derived from other genetic loci in an organism, but having substantial homology to the carboxypeptidase of SEQ ID NO 1. Variants also include proteins substantially homologous to the carboxypeptidase but derived from another organism, i.e., an ortholog. Variants also include proteins that are substantially homologous to the carboxypeptidase that are produced by chemical synthesis. Variants also include proteins that are substantially homologous to the carboxypeptidase that are produced by recombinant methods. It is understood, however, that variants exclude any amino acid sequences disclosed prior to the invention.

As used herein, two proteins (or a region of the proteins) are substantially homologous when the amino acid sequences are at least about 50–55%, 55–60%, 60–65%, 65–70%, 70–75%, typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in SEQ ID NO 2 under stringent conditions as more fully described below.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the amino acid sequences herein having 502 amino acid residues, at least 165, preferably at least 200, more preferably at least 250, even more preferably at least 300, and even more preferably at least 350, 400, 450, and 500 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the carboxypeptidase. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., *Science* 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

A preferred, non-limiting example of such a mathematical algorithm is described in Karlin et al. (1993) *Proc. Natl. Acad. Sci.* USA 90:5873–5877. Such an algorithm is incorporated into the NBLAST and XBLAST programs (version 2.0) as described in Altschul et al. (1997) *Nucleic Acids Res.* 25:3389–3402. When utilizing BLAST and Gapped BLAST programs, the default parameters of the respective programs (e.g., NBLAST) can be used. See www.ncbi.nlm.nih.gov. In one embodiment, parameters for sequence comparison can be set at score=100, wordlength=12, or can be varied (e.g., W=5 or W=20).

In a preferred embodiment, the percent identity between two amino acid sequences is determined using the Needleman et al. (1970) (*J. Mol. Biol.* 48:444–453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux et al. (1984) *Nucleic Acids Res.* 12(1):387) (available at www.gcg.com), using a NWSgapdna.CMP matrix and a gap weight of 40, 50, 60, 70, or 80 and a length weight of 1, 2, 3, 4, 5, or 6.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis et al. (1994) *Comput. Appl. Biosci.* 10:3–5; and FASTA described in Pearson et al. (1988) *PNAS* 85:2444–8.

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the regions relating to peptide binding, specificity, or hydrolysis, regulatory/allosteric regions, regions involved in membrane association, regions involved in modification or activation of the carboxypeptidase, such as glycosylation, phosphorylation, and myristoylation, and any metal binding regions.

Fully functional variants typically contain only conservative variation or variation in non-critical residues or in non-critical regions. Functional variants can also contain substitution of similar amino acids, which results in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

As indicated, variants can be naturally-occurring or can be made by recombinant means or chemical synthesis to provide useful and novel characteristics for the carboxypeptidase polypeptide. This includes preventing immunogenicity from pharmaceutical formulations by preventing protein aggregation.

Useful variations further include alteration of catalytic activity. For example, one embodiment involves a variation at the binding site that results in binding but not hydrolysis, or slower hydrolysis, of substrate. A further useful variation at the same site can result in altered affinity for substrate. Useful variations also include changes that provide for affinity for another substrate. Another useful variation includes one that prevents modification of the carboxypeptidase. Another useful variation includes variation in the region that provides for altered membrane association. Another useful variation provides a fusion protein in which one or more regions are operationally fused to one or more regions from another carboxypeptidase.

Amino acids that are essential for function can be identified by methods known in the art, such as site-directed mutagenesis or alanine-scanning mutagenesis (Cunningham et al. (1985) *Science* 244:1081–1085). The latter procedure introduces single alanine mutations at every residue in the molecule. The resulting mutant molecules are then tested for biological activity, such as peptide hydrolysis in vitro or peptide-dependent in vitro activity, such as proliferative activity. Sites that are critical for binding can also be determined by structural analysis such as crystallization, nuclear magnetic resonance or photoaffinity labeling (Smith et al. (1992) *J. Mol. Biol.* 224:899-904; de Vos et al. (1992) *Science* 255:306–312).

Substantial homology can be to the entire nucleic acid or amino acid sequence or to fragments of these sequences.

The invention thus also includes polypeptide fragments of the carboxypeptidase. Fragments can be derived from the amino acid sequence shown in SEQ ID NO 1. However, the invention also encompasses fragments of the variants of the carboxypeptidase as described herein.

The fragments to which the invention pertains, however, are not to be construed as encompassing fragments that may be disclosed prior to the present invention.

Accordingly, a fragment can comprise at least about 11, 12, 13, 14, 15, 20, 25, 30, 35, 40, 45, 50 or more contiguous amino acids. Fragments can retain one or more of the biological activities of the protein, for example the ability to bind to or hydrolyze peptides, as well as fragments that can be used as an immunogen to generate carboxypeptidase antibodies.

Biologically active fragments (peptides which are, for example, 5, 7, 10, 12, 15, 20, 30, 35, 36, 37, 38, 39, 40, 50, 100 or more amino acids in length) can comprise a region or motif, e.g., regions relating to peptide binding, specificity, or hydrolysis, regulatory/allosteric regions, regions involved in membrane association, regions involved in modification or activation of the carboxypeptidase, such as glycosylation, phosphorylation, and myristoylation, and any metal binding regions.

Such regions or motifs can be identified by means of routine computerized homology searching procedures.

Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the region or domain from which they are derived.

These regions can be identified by well-known methods involving computerized homology analysis.

The invention also provides fragments with immunogenic properties. These contain an epitope-bearing portion of the carboxypeptidase and variants. These epitope-bearing peptides are useful to raise antibodies that bind specifically to a carboxypeptidase polypeptide or region or fragment. These peptides can contain at least 10, 12, at least 14, or between at least about 15 to about 30 amino acids.

Non-limiting examples of antigenic polypeptides that can be used to generate antibodies include but are not limited to peptides derived from an extracellular region. Regions having a high antigenicity index are shown in FIG. 3. However, intracellularly-made antibodies ("intrabodies") are also encompassed, which would recognize intracellular peptide regions.

The epitope-bearing carboxypeptidase polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the carboxypeptidase fragment and an additional region fused to the carboxyl terminus of the fragment.

The invention thus provides chimeric or fusion proteins. These comprise a carboxypeptidase peptide sequence operatively linked to a heterologous peptide having an amino acid sequence not substantially homologous to the carboxypeptidase. "Operatively linked" indicates that the carboxypeptidase peptide and the heterologous peptide are fused in-frame. The heterologous peptide can be fused to the N-terminus or C-terminus of the carboxypeptidase or can be internally located.

In one embodiment the fusion protein does not affect carboxypeptidase function per se. For example, the fusion protein can be a GST-fusion protein in which the carboxypeptidase sequences are fused to the C-terminus of the GST sequences. Other types of fusion proteins include, but are not limited to, enzymatic fusion proteins, for example beta-galactosidase fusions, yeast two-hybrid GAL4 fusions, poly-His fusions and Ig fusions. Such fusion proteins, particularly poly-His fusions, can facilitate the purification of recombinant carboxypeptidase. In certain host cells (e.g., mammalian host cells), expression and/or secretion of a protein can be increased by using a heterologous signal sequence. Therefore, in another embodiment, the fusion protein contains a heterologous signal sequence at its N-terminus.

EP-A-O 464 533 discloses fusion proteins comprising various portions of immunoglobulin constant regions. The Fc is useful in therapy and diagnosis and thus results, for example, in improved pharmacokinetic properties (EP-A 0232 262). In drug discovery, for example, human proteins have been fused with Fc portions for the purpose of high-throughput screening assays to identify antagonists (Bennett et al. (1995) *J. Mol. Recog.* 8:52–58 (1995) and Johanson et al. *J. Biol. Chem.* 270:9459–9471). Thus, this invention also encompasses soluble fusion proteins containing a carboxypeptidase polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa.

A chimeric or fuision protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al. (1992) *Current Protocols in Molecular Biology*). Moreover, many expression vectors are commercially available that already encode a fusion moiety (e.g., a GST protein). A carboxypeptidase-encoding nucleic acid can be cloned into such an expression vector such that the fusion moiety is linked in-frame to the carboxypeptidase.

Another form of fusion protein is one that directly affects carboxypeptidase functions. Accordingly, a carboxypeptidase polypeptide is encompassed by the present invention in which one or more of the carboxypeptidase regions (or parts thereof) has been replaced by homologous regions (or parts thereof) from another carboxypeptidase. Accordingly, various permutations are possible. For example, the active site region, or subregion thereof, can be replaced with the active site region or subregion from another carboxypeptidase. As a further example, the membrane-associated region, or parts thereof, can be replaced. Thus, chimeric carboxypeptidases can be formed in which one or more of the native regions has been replaced by another.

It is understood, however, that sites could be derived from carboxypeptidases that occur in the mammalian genome but which have not yet been discovered or characterized. Such sites include, but are not limited to, regions relating to peptide binding, specificity, or hydrolysis, regulatory/ allosteric regions, regions involved in membrane association, regions involved in modification or activation of the carboxypeptidase, such as glycosylation, phosphorylation, and myristoylation, and any metal binding regions, and any other functional site disclosed herein.

The isolated carboxypeptidase protein can be purified from cells that naturally express it, such as from those disclosed herein, especially purified from cells that have been altered to express it (recombinant), or synthesized using known protein synthesis methods. Preferred tissues in which the carboxypeptidase is expressed include, but are not limited to, prostate, breast, skeletal muscle, brain, testis, and thyroid. Cells also include colon, breast, and lung carcinoma.

In one embodiment, the protein is produced by recombinant DNA techniques. For example, a nucleic acid molecule encoding the carboxypeptidase polypeptide is cloned into an expression vector, the expression vector introduced into a host cell and the protein expressed in the host cell. The protein can then be isolated from the cells by an appropriate purification scheme using standard protein purification techniques.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art.

Accordingly, the polypeptides also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (1990) *Meth. Enzymol.* 182: 626–646) and Rattan et al. (1992) *Ann. N.Y. Acad. Sci.* 663:48–62).

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods.

Modifications can occur anywhere in a polypeptide, including the peptide backbone, the amino acid side-chains and the amino or carboxyl termini. Blockage of the amino or carboxyl group in a polypeptide, or both, by a covalent modification, is common in naturally-occurring and synthetic polypeptides. For instance, the aminoterminal residue of polypeptides made in *E. coli*, prior to proteolytic processing, almost invariably will be N-formylmethionine.

The modifications can be a function of how the protein is made. For recombinant polypeptides, for example, the modifications will be determined by the host cell posttranslational modification capacity and the modification signals in the polypeptide amino acid sequence. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

The same type of modification may be present in the same or varying degree at several sites in a given polypeptide. Also, a given polypeptide may contain more than one type of modification.

Polypeptide Uses

The protein sequences of the present invention can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See www.ncbi.nlm.nih.gov.

The carboxypeptidase polypeptides are useful for producing antibodies specific for the carboxypeptidase, regions, or fragments. Regions having a high antigenicity index score are shown in FIG. 3.

The carboxypeptidase polypeptides are useful for biological assays related to carboxypeptidases. Such assays involve any of the known carboxypeptidase functions or activities or properties useful for diagnosis and treatment of carboxypeptidase-related conditions.

The carboxypeptidase polypeptides are also useful in drug screening assays, in cell-based or cell-free systems. Cell-based systems can be native, i.e., cells that normally express the carboxypeptidase, as a biopsy or expanded in cell culture. In one embodiment, however, cell-based assays involve recombinant host cells expressing the carboxypeptidase.

Determining the ability of the test compound to interact with the carboxypeptidase can also comprise determining the ability of the test compound to preferentially bind to the polypeptide as compared to the ability of a known binding molecule to bind to the polypeptide.

The polypeptides can be used to identify compounds that modulate carboxypeptidase activity. Such compounds, for example, can increase or decrease affinity or rate of binding to substrate, compete with substrate for binding to the carboxypeptidase, or displace substrate bound to the carboxypeptidase. Both carboxypeptidase and appropriate variants and fragments can be used in high-throughput screens to assay candidate compounds for the ability to bind to the carboxypeptidase. These compounds can be fuirther screened against a functional carboxypeptidase to determine the effect of the compound on the carboxypeptidase activity. Compounds can be identified that activate (agonist) or inactivate (antagonist) the carboxypeptidase to a desired degree. Modulatory methods can be performed in vitro (e.g., by culturing the cell with the agent) or, alternatively, in vivo (e.g., by administering the agent to a subject).

The carboxypeptidase polypeptides can be used to screen a compound for the ability to stimulate or inhibit interaction between the carboxypeptidase protein and a target molecule that normally interacts with the carboxypeptidase protein. The assay includes the steps of combining the carboxypeptidase protein with a candidate compound under conditions that allow the carboxypeptidase protein or fragment to interact with the target molecule, and to detect the formation of a complex between the carboxypeptidase protein and the target or to detect the biochemical consequence of the interaction with the carboxypeptidase and the target, such as any of the associated effects of peptide hydrolysis.

Determining the ability of the carboxypeptidase to bind to a target molecule can also be accomplished using a technology such as real-time Bimolecular Interaction Analysis (BIA). Sjolander et al. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore™). Changes in the optical phenomenon surface plasmon resonance (SPR) can be used as an indication of real-time reactions between biological molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer or small molecule libraries of compounds (Lam, K. S. (1997) *Anticancer DrugDes.* 12:145).

Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233. Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 97:6378–6382); (Felici (1991) *J. Mol. Biol.* 222:301–310); (Ladner supra).

Candidate compounds include, for example, 1) peptides such as soluble peptides, including Ig-tailed fusion peptides and members of random peptide libraries (see, e.g., Lam et al. (1991) *Nature* 354:82–84; Houghten et al. (1991) *Nature* 354:84–86) and combinatorial chemistry-derived molecular libraries made of D- and/or L- configuration amino acids; 2) phosphopeptides (e.g., members of random and partially degenerate, directed phosphopeptide libraries, see, e.g., Songyang et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble full-length carboxypeptidase or fragment that competes for substrate binding. Other candidate compounds include mutant carboxypeptidases or appropriate fragments containing mutations that affect carboxypeptidase function and thus compete for substrate. Accordingly, a fragment that competes for substrate, for example with a higher affinity, or a fragment that binds the substrate but does not degrade it, is encompassed by the invention.

The invention provides other end points to identify compounds that modulate (stimulate or inhibit) carboxypeptidase activity. The assays typically involve an assay of cellular events that indicate carboxypeptidase activity. Thus, the expression of genes that are up- or down-regulated in response to carboxypeptidase activity can be assayed. In one embodiment, the regulatory region of such genes can be operably linked to a marker that is easily detectable, such as luciferase. Alternatively, modification of the carboxypeptidase could also be measured.

Any of the biological or biochemical functions mediated by the carboxypeptidase can be used as an endpoint assay. These include all of the biochemical or biochemical/biological events described herein, in the references cited herein, incorporated by reference for these endpoint assay targets, and other functions known to those of ordinary skill in the art.

In the case of the carboxypeptidase, assays for specific end points can include assays for peptide hydrolysis (e.g., amino acid production or change in substrate peptide size).

Binding and/or activating compounds can also be screened by using chimeric carboxypeptidase proteins in which one or more regions/domains, segments, sites, and the like, as disclosed herein, or parts thereof, can be replaced by their heterologous counterparts derived from other carboxypeptidases. For example, a catalytic region can be used that interacts with a different specificity and/or affinity than the native carboxypeptidase. Accordingly, a different set of cellular components is available as an end-point assay for activation. Alternatively, a membrane-associated portion or subregions can be replaced with the membrane portion or subregions specific to a host cell that is different from the host cell from which the native carboxypeptidase is derived. This allows for assays to be performed in other than the specific host cell from which the carboxypeptidase is derived. Alternatively, a heterologous substrate recognition sequence can replace the native sequence. This can result in having an effect on a different cellular pathway. Accordingly, a different set of cellular components is available as an endpoint assay for activation. Activation can also be detected by a reporter gene containing an easily detectable coding region operably linked to a transcriptional regulatory sequence that is part of the native pathway.

The carboxypeptidase polypeptides are also useful in competition binding assays in methods designed to discover compounds that interact with the carboxypeptidase. Thus, a compound is exposed to a carboxypeptidase polypeptide under conditions that allow the compound to bind or to otherwise interact with the polypeptide. Soluble carboxypeptidase polypeptide is also added to the mixture. If the test compound interacts with the soluble carboxypeptidase polypeptide, it decreases the amount of complex formed or activity from the carboxypeptidase target. This type of assay is particularly useful in cases in which compounds are sought that interact with specific regions of the carboxypeptidase. Thus, the soluble polypeptide that competes with the target carboxypeptidase region is designed to contain peptide sequences corresponding to the region of interest.

Another type of competition-binding assay can be used to discover compounds that interact with specific functional sites. As an example, peptide substrate and a candidate compound can be added to a sample of the carboxypeptidase. Compounds that interact with the carboxypeptidase at the same site as the peptide will reduce the amount of complex formed between the carboxypeptidase and the peptide. Accordingly, it is possible to discover a compound that specifically prevents interaction between the carboxypeptidase and the peptide. Another example involves adding a candidate compound to a sample of carboxypeptidase and peptide substrate. A compound that competes with the peptide substrate will reduce the amount of hydrolysis or binding of the substrate to the carboxypeptidase. Accordingly, compounds can be discovered that directly interact with the carboxypeptidase and compete with the substrate. Such assays can involve any other component that interacts with the carboxypeptidase.

To perform cell free drug screening assays, it is desirable to immobilize either the carboxypeptidase, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/carboxypeptidase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes is dissociated. Alternatively, the complexes can be dissociated from the matrix, separated by SDS-PAGE, and the level of carboxypeptidase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a carboxypeptidase-binding target component, such as peptide substrate, and a candidate compound are incubated in the carboxypeptidase-presenting wells and the amount of complex trapped in the well can be quantitated. Methods for detecting such complexes, in addition to those described above for the GST-immobilized complexes, include immunodetection of complexes using antibodies reactive with the carboxypeptidase target molecule, or which are reactive with carboxypeptidase and compete with the target molecule; as well as enzyme-linked assays which rely on detecting an enzymatic activity associated with the target molecule.

Modulators of carboxypeptidase activity identified according to these drug screening assays can be used to treat a subject with a disorder related to the carboxypeptidase, by treating cells that express the carboxypeptidase, such as those disclosed here. Preferred tissues in which the carboxypeptidase is expressed include, but are not limited to, prostate, breast, skeletal muscle, brain, testes, thyroid, and fetal liver, kidney, and heart. Further, preferred tissues include, but are not limited to, colon and breast carcinoma, and lung carcinoma, especially squamous cell carcinoma. In addition, this carboxypeptidase is overexpressed in breast, lung and colon tumors as disclosed herein. Accordingly, expression of the carboxypeptidase is especially relevant to cancer treatment, including invasion and metastasis. These methods of treatment include the steps of administering the modulators of carboxypeptidase activity in a pharmaceutical composition as described herein, to a subject in need of such treatment.

Further disorders in which the carboxypeptidase expression is relevant include, but are not limited to, any disorders involving the cells in which the carboxypeptidase is expressed as disclosed herein.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the brain include, but are limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

The carboxypeptidase polypeptides are thus useful for treating a carboxypeptidase-associated disorder characterized by aberrant expression or activity of a carboxypeptidase. In one embodiment, the method involves administering an agent (e.g., an agent identified by a screening assay described herein), or combination of agents that modulates (e.g., upregulates or downregulates) expression or activity of the protein. In another embodiment, the method involves administering the carboxypeptidase as therapy to compensate for reduced or aberrant expression or activity of the protein.

Methods for treatment include but are not limited to the use of soluble carboxypeptidase or fragments of the carboxypeptidase protein that compete for substrate. These carboxypeptidases or fragments can have a higher affinity for the target so as to provide effective competition.

Stimulation of activity is desirable in situations in which the protein is abnormally downregulated and/or in which increased activity is likely to have a beneficial effect. Likewise, inhibition of activity is desirable in situations in which the protein is abnormally upregulated and/or in which decreased activity is likely to have a beneficial effect. In one example of such a situation, a subject has a disorder characterized by aberrant development or cellular differentiation. In another example, the subject has a proliferative disease (e.g., cancer) or a disorder characterized by an aberrant hematopoietic response. In another example, it is desirable to achieve tissue regeneration in a subject (e.g., where a subject has undergone brain or spinal cord injury and it is desirable to regenerate neuronal tissue in a regulated manner).

In yet another aspect of the invention, the proteins of the invention can be used as "bait proteins" in a two-hybrid assay or three-hybrid assay (see, e.g., U.S. Pat. No. 5,283, 317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins (captured proteins) which bind to or interact with the proteins of the invention and modulate their activity.

The carboxypeptidase polypeptides also are useful to provide a target for diagnosing a disease or predisposition to disease related to the carboxypeptidase, including, but not limited to, those diseases discussed herein, and particularly breast, colon and lung carcinoma. Targets are useful for diagnosing a disease or predisposition to disease mediated by the carboxypeptidase, especially in the tissues shown in those found herein, especially in prostate, breast, skeletal muscle, brain, testis, thyroid, and carcinomas, such as in colon, breast, and lung. Accordingly, methods are provided for detecting the presence, or levels of, the carboxypeptidase in a cell, tissue, or organism. The method involves contacting a biological sample with a compound capable of interacting with the carboxypeptidase such that the interaction can be detected.

One agent for detecting carboxypeptidase is an antibody capable of selectively binding to carboxypeptidase. A biological sample includes tissues, cells and biological fluids isolated from a subject, as well as tissues, cells and fluids present within a subject.

The carboxypeptidase also provides a target for diagnosing active disease, or predisposition to disease, in a patient having a variant carboxypeptidase. Thus, carboxypeptidase can be isolated from a biological sample and assayed for the presence of a genetic mutation that results in an aberrant protein. This includes amino acid substitution, deletion, insertion, rearrangement, (as the result of aberrant splicing events), and inappropriate post-translational modification. Analytic methods include altered electrophoretic mobility, altered tryptic peptide digest, altered carboxypeptidase activity in cell-based or cell-free assay, alteration in substrate binding or degradation, antibody-binding pattern, altered isoelectric point, direct amino acid sequencing, and any other of the known assay techniques useful for detecting mutations in a protein in general or in a carboxypeptidase specifically.

In vitro techniques for detection of carboxypeptidase include enzyme linked immunosorbent assays (ELISAs), Western blots, immunoprecipitations and immunofluorescence. Alternatively, the protein can be detected in vivo in a subject by introducing into the subject a labeled anti-carboxypeptidase antibody. For example, the antibody can be labeled with a radioactive marker whose presence and location in a subject can be detected by standard imaging techniques. Particularly useful are methods, which detect the allelic variant of the carboxypeptidase expressed in a subject, and methods, which detect fragments of the carboxypeptidase in a sample.

The carboxypeptidase polypeptides are also useful in pharmacogenomic analysis. Pharmacogenomics deal with clinically significant hereditary variations in the response to drugs due to altered drug disposition and abnormal action in affected persons. See, e.g., Eichelbaum, M. (1996) Clin. Exp. Pharmacol. Physiol. 23(10–11):983–985, and Linder, M. W. (1997) Clin. Chem. 43(2):254–266. The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes affects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the carboxypeptidase in which one or more of the carboxypeptidase functions in one population is different from those in another population. The polypeptides thus allow a target to ascertain a genetic predisposition that can affect treatment modality. Thus, in a peptide-based treatment, polymorphism may give rise to catalytic regions that are more or less active. Accordingly, dosage would necessarily be modified to maximize the therapeutic effect within a given population containing the polymorphism. As an alternative to genotyping, specific polymorphic polypeptides could be identified.

The carboxypeptidase polypeptides are also useful for monitoring therapeutic effects during clinical trials and other treatment. Thus, the therapeutic effectiveness of an agent that is designed to increase or decrease gene expression, protein levels or carboxypeptidase activity can be monitored over the course of treatment using the carboxypeptidase polypeptides as an end-point target. The monitoring can be, for example, as follows: (i) obtaining a pre-administration sample from a subject prior to administration of the agent; (ii) detecting the level of expression or activity of the protein in the pre-administration sample; (iii) obtaining one or more post-administration samples from the subject; (iv) detecting the level of expression or activity of the protein in the post-administration samples; (v) comparing the level of expression or activity of the protein in the pre-administration sample with the protein in the post-administration sample or samples; and (vi) increasing or decreasing the administration of the agent to the subject accordingly.

Antibodies

The invention also provides antibodies that selectively bind to the carboxypeptidase and its variants and fragments. An antibody is considered to selectively bind, even if it also binds to other proteins that are not substantially homologous with the carboxypeptidase. These other proteins share homology with a fragment or domain of the carboxypeptidase. This conservation in specific regions gives rise to antibodies that bind to both proteins by virtue of the homologous sequence. In this case, it would be understood that antibody binding to the carboxypeptidase is still selective.

To generate antibodies, an isolated carboxypeptidase polypeptide is used as an immunogen to generate antibodies using standard techniques for polyclonal and monoclonal antibody preparation. Either the full-length protein or antigenic peptide fragment can be used. Regions having a high antigenicity index are shown in FIG. 3.

Antibodies are preferably prepared from these regions or from discrete fragments in these regions. However, antibodies can be prepared from any region of the peptide as described herein. A preferred fragment produces an antibody that diminishes or completely prevents substrate hydrolysis or binding. Antibodies can be developed against the entire carboxypeptidase or regions/domains of the carboxypeptidase as described herein. Antibodies can also be developed against specific functional sites as disclosed herein.

The antigenic peptide can comprise a contiguous sequence of at least 12, 14, 15, or 30 amino acid residues. In one embodiment, fragments correspond to regions that are located on the surface of the protein, e.g., hydrophilic regions. These fragments are not to be construed, however, as encompassing any fragments, which may be disclosed prior to the invention.

Antibodies can be polyclonal or monoclonal. An intact antibody, or a fragment thereof (e.g. Fab or F(ab')$_2$) can be used.

Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

An appropriate immunogenic preparation can be derived from native, recombinantly expressed, or chemically synthesized peptides.

Antibody Uses

The antibodies can be used to isolate a carboxypeptidase by standard techniques, such as affinity chromatography or immunoprecipitation. The antibodies can facilitate the purification of the natural carboxypeptidase from cells and recombinantly produced carboxypeptidase expressed in host cells.

The antibodies are useful to detect the presence of carboxypeptidase in cells or tissues to determine the pattern of expression of the carboxypeptidase among various tissues in an organism and over the course of normal development.

The antibodies can be used to detect carboxypeptidase in situ, in vitro, or in a cell lysate or supernatant in order to evaluate the abundance and pattern of expression.

The antibodies can be used to assess abnormal tissue distribution or abnormal expression during development.

Antibody detection of circulating fragments of the full length carboxypeptidase can be used to identify carboxypeptidase turnover.

Further, the antibodies can be used to assess carboxypeptidase expression in disease states such as in active stages of the disease or in an individual with a predisposition toward disease related to carboxypeptidase function. When a disorder is caused by an inappropriate tissue distribution, developmental expression, or level of expression of the carboxypeptidase protein, the antibody can be prepared against the normal carboxypeptidase protein. If a disorder is characterized by a specific mutation in the carboxypeptidase, antibodies specific for this mutant protein can be used to assay for the presence of the specific mutant carboxypeptidase. However, intracellularly-made antibodies ("intrabodies") are also encompassed, which would recognize intracellular carboxypeptidase peptide regions.

The antibodies can also be used to assess normal and aberrant subcellular localization of cells in the various tissues in an organism. Antibodies can be developed against the whole carboxypeptidase or portions of the carboxypeptidase, for example, the catalytic region.

The diagnostic uses can be applied, not only in genetic testing, but also in monitoring a treatment modality. Accordingly, where treatment is ultimately aimed at correcting carboxypeptidase expression level or the presence of aberrant carboxypeptidases and aberrant tissue distribution or developmental expression, antibodies directed against the carboxypeptidase or relevant fragments can be used to monitor therapeutic efficacy.

Antibodies accordingly can be used diagnostically to monitor protein levels in tissue as part of a clinical testing procedure, e.g., to, for example, determine the efficacy of a given treatment regimen.

Additionally, antibodies are useful in pharmacogenomic analysis. Thus, antibodies prepared against polymorphic carboxypeptidase can be used to identify individuals that require modified treatment modalities.

The antibodies are also useful as diagnostic tools as an immunological marker for aberrant carboxypeptidase analyzed by electrophoretic mobility, isoelectric point, tryptic peptide digest, and other physical assays known to those in the art.

The antibodies are also useful for tissue typing. Thus, where a specific carboxypeptidase has been correlated with expression in a specific tissue, antibodies that are specific for this carboxypeptidase can be used to identify a tissue type.

The antibodies are also useful in forensic identification. Accordingly, where an individual has been correlated with a specific genetic polymorphism resulting in a specific polymorphic protein, an antibody specific for the polymorphic protein can be used as an aid in identification.

The antibodies are also useful for inhibiting carboxypeptidase function, for example, blocking the catalytic site.

These uses can also be applied in a therapeutic context in which treatment involves inhibiting carboxypeptidase function. An antibody can be used, for example, to block peptide substrate binding. Antibodies can be prepared against specific fragments containing sites required for function or against intact carboxypeptidase associated with a cell.

Completely human antibodies are particularly desirable for therapeutic treatment of human patients. For an overview of this technology for producing human antibodies, see Lonberg et al. (1995) *Int. Rev. Immunol.* 13:65–93. For a detailed discussion of this technology for producing human antibodies and human monoclonal antibodies and protocols for producing such antibodies, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

The invention also encompasses kits for using antibodies to detect the presence of a carboxypeptidase protein in a biological sample. The kit can comprise antibodies such as a labeled or labelable antibody and a compound or agent for detecting carboxypeptidase in a biological sample; means for determining the amount of carboxypeptidase in the sample; and means for comparing the amount of carboxypeptidase in the sample with a standard. The compound or agent can be packaged in a suitable container. The kit can further comprise instructions for using the kit to detect carboxypeptidase.

Polynucleotides

The nucleotide sequences in SEQ ID NO 2 were obtained by sequencing the deposited human cDNA. Accordingly, the sequence of the deposited clone is controlling as to any discrepancies between the two and any reference to the sequence of SEQ ID NO 2 includes reference to the sequence of the deposited cDNA.

The specifically disclosed cDNA comprises the coding region and 5' and 3' untranslated sequences in SEQ ID NO 2.

The nucleic acid is expressed in those tissues as disclosed herein. In particular, the carboxypeptidase is expressed in prostate, breast, skeletal muscle, brain, testis, thyroid, and carcinomas, such as in colon, breast, and lung. In addition, this carboxypeptidase is overexpressed in a number of breast, lung and colon tumor lines as disclosed herein.

The invention provides isolated polynucleotides encoding the novel carboxypeptidases. The term "carboxypeptidase polynucleotide" or "carboxypeptidase nucleic acid" refers to the sequence shown in SEQ ID NO 2 or in the deposited cDNA. The term "carboxypeptidase polynucleotide" or "carboxypeptidase nucleic acid" fuirther includes variants and fragments of the carboxypeptidase polynucleotides.

An "isolated" carboxypeptidase nucleic acid is one that is separated from other nucleic acid present in the natural source of the carboxypeptidase nucleic acid. Preferably, an "isolated" nucleic acid is free of sequences which naturally flank the carboxypeptidase nucleic acid (i.e., sequences located at the 5' and 3' ends of the nucleic acid) in the genomic DNA of the organism from which the nucleic acid is derived. However, there can be some flanking nucleotide sequences, for example up to about 5 KB. The important point is that the carboxypeptidase nucleic acid is isolated from flanking sequences such that it can be subjected to the specific manipulations described herein, such as recombinant expression, preparation of probes and primers, and other uses specific to the carboxypeptidase nucleic acid sequences.

Moreover, an "isolated" nucleic acid molecule, such as a cDNA or RNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

In some instances, the isolated material will form part of a composition (for example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

In some instances, the isolated material will form part of a composition (or example, a crude extract containing other substances), buffer system or reagent mix. In other circumstances, the material may be purified to essential homogeneity, for example as determined by PAGE or column chromatography such as HPLC. Preferably, an isolated nucleic acid comprises at least about 50, 80 or 90% (on a molar basis) of all macromolecular species present.

The carboxypeptidase polynucleotides can encode the mature protein plus additional amino or carboxyterminal amino acids, or amino acids interior to the mature polypeptide (when the mature form has more than one polypeptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

The carboxypeptidase polynucleotides include, but are not limited to, the sequence encoding the mature polypeptide alone, the sequence encoding the mature polypeptide and additional coding sequences, such as a leader or secretory sequence (e.g., a pre-pro or pro-protein sequence), the sequence encoding the mature polypeptide, with or without the additional coding sequences, plus additional non-coding sequences, for example introns and non-coding 5' and 3' sequences such as transcribed but non-translated sequences that play a role in transcription, RNA processing (including splicing and polyadenylation signals), ribosome binding and stability of mRNA. In addition, the polynucleotide may be fused to a marker sequence encoding, for example, a peptide that facilitates purification.

Carboxypeptidase polynucleotides can be in the form of RNA, such as RNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

Carboxypeptidase nucleic acid can comprise the nucleotide sequences shown in SEQ ID NO 2, corresponding to human osteoblast or brain cDNA.

In one embodiment, the carboxypeptidase nucleic acid comprises only the coding region.

The invention further provides variant carboxypeptidase polynucleotides, and fragments thereof, that differ from the nucleotide sequence shown in SEQ ID NO 2 due to degeneracy of the genetic code and thus encode the same protein as that encoded by the nucleotide sequence shown in SEQ ID NO 2.

The invention also provides carboxypeptidase nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Typically, variants have a substantial identity with a nucleic acid molecules of SEQ ID NO 2 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a carboxypeptidase that is typically at least about 50–55%, 55–60%, 60–65%, 65–70%, 70–75%, more typically at least about 80–85%, and most typically at least about 90–95% or more homologous to the nucleotide sequence shown in SEQ ID NO 2 or a fragment of this sequence. Such nucleic acid molecules can readily be identified as being able to hybridize under stringent conditions, to the nucleotide sequence shown in SEQ ID NO 2 or a fragment of the sequence. It is understood that stringent hybridization does not indicate substantial homology where it is due to general homology, such as poly A sequences, or sequences common to all or most proteins, all carboxypeptidases, all prolyl carboxypeptidases or all seryl carboxypeptidases. Moreover, it is understood that variants do not include any of the nucleic acid sequences that may have been disclosed prior to the invention.

As used herein, the term "hybridizes under stringent conditions" is intended to describe conditions for hybridization and washing under which nucleotide sequences encoding a polypeptide at least about 50–55% homologous to each other typically remain hybridized to each other. The conditions can be such that sequences at least about 60–65%, at least about 70%, at least about 75%, at least about 80%, at least about 90%, at least about 95% or more identical to each other remain hybridized to one another. Such stringent conditions are known to those skilled in the art and can be found in *Current Protocols in Molecular Biology*, John Wiley & Sons, N.Y. (1989), 6.3.1–6.3.6, incorporated by reference. One example of stringent hybridization conditions are hybridization in 6X sodium chloride/sodium citrate (SSC) at about 45° C., followed by one or more washes in 0.2×SSC, 0.1% SDS at 50–65° C. In another non-limiting example, nucleic acid molecules are allowed to hybridize in 6×sodium chloride/sodium citrate (SSC) at about 45° C., followed by one or more low stringency washes in 0.2×SSC/0.1% SDS at room temperature, or by one or more moderate stringency washes in 0.2×SSC/0.1% SDS at 42° C., or washed in 0.2×SSC/0.1% SDS at 65° C. for high stringency. In one embodiment, an isolated nucleic acid molecule that hybridizes under stringent conditions to the sequence of SEQ ID NO 1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

As understood by those of ordinary skill, the exact conditions can be determined empirically and depend on ionic strength, temperature and the concentration of destabilizing agents such as formamide or denaturing agents such as SDS. Other factors considered in determining the desired hybridization conditions include the length of the nucleic acid sequences, base composition, percent mismatch between the hybridizing sequences and the frequency of occurrence of subsets of the sequences within other non-identical sequences. Thus, equivalent conditions can be determined by varying one or more of these parameters while maintaining a similar degree of identity or similarity between the two nucleic acid molecules.

The present invention also provides isolated nucleic acids that contain a single or double stranded fragment or portion that hybridizes under stringent conditions to the nucleotide sequence of SEQ ID NO 2 or the complement of SEQ ID NO 2. In one embodiment, the nucleic acid consists of a portion of the nucleotide sequence of SEQ ID NO 2 and the complement of SEQ ID NO 2. The nucleic acid fragments of the invention are at least about 15, preferably at least about 18, 20, 23 or 25 nucleotides, and can be 30, 40, 50, 100, 200, 500 or more nucleotides in length. Longer fragments, for example, 30 or more nucleotides in length, which encode antigenic proteins or polypeptides described herein are useful.

As discussed, the invention provides polynucleotides that comprise a fragment of the full-length carboxypeptidase polynucleotides. The fragment can be single or double-stranded and can comprise DNA or RNA. The fragment can be derived from either the coding or the non-coding sequence.

In another embodiment an isolated carboxypeptidase nucleic acid encodes the entire coding region. In another embodiment the isolated carboxypeptidase nucleic acid encodes a sequence corresponding to the mature protein that may be from about amino acid 6 to the last amino acid. Other fragments include nucleotide sequences encoding the amino acid fragments described herein.

Thus, carboxypeptidase nucleic acid fragments further include sequences corresponding to the regions/domains described herein, subregions also described, and specific functional sites. Carboxypeptidase nucleic acid fragments also include combinations of the regions/domains, segments, and other functional sites described above. A person of ordinary skill in the art would be aware of the many permutations that are possible.

Where the location of the domains or sites have been predicted by computer analysis, one of ordinary sill would appreciate that the amino acid residues constituting these domains can vary depending on the criteria used to define the domains.

However, it is understood that a carboxypeptidase fragment includes any nucleic acid sequence that does not include the entire gene.

The invention also provides carboxypeptidase nucleic acid fragments that encode epitope bearing regions of the carboxypeptidase proteins described herein.

Fragments from about 1–660 can comprise about 5, 10, 15, 20, 25, 30, 35, 40, 45, 50, 75, 100, 150, 200, 250, 300, 350, or more nucleotides.

Nucleic acid fragments, according to the present invention, are not to be construed as encompassing those fragments that may have been disclosed prior to the invention.

Polynucleotide Uses

The nucleotide sequences of the present invention can be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403–10. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The nucleic acid fragments of the invention provide probes or primers in assays such as those described below. "Probes" are oligonucleotides that hybridize in a base-specific manner to a complementary strand of nucleic acid. Such probes include polypeptide nucleic acids, as described in Nielsen et al. (1991) *Science* 254:1497–1500. Typically, a probe comprises a region of nucleotide sequence that hybridizes under highly stringent conditions to at least about 15, typically about 20–25, and more typically about 40, 50 or 75 consecutive nucleotides of the nucleic acid sequence shown in SEQ ID NO 2 and the complements thereof. More typically, the probe further comprises a label, e.g., radioisotope, fluorescent compound, enzyme, or enzyme co-factor.

As used herein, the term "primer" refers to a single-stranded oligonucleotide which acts as a point of initiation of template-directed DNA synthesis using well-known methods (e.g., PCR, LCR) including, but not limited to those described herein. The appropriate length of the primer depends on the particular use, but typically ranges from about 15 to 30 nucleotides. The term "primer site" refers to the area of the target DNA to which a primer hybridizes. The term "primer pair" refers to a set of primers including a 5' (upstream) primer that hybridizes with the 5' end of the nucleic acid sequence to be amplified and a 3' (downstream) primer that hybridizes with the complement of the sequence to be amplified.

The carboxypeptidase polynucleotides are thus useful for probes, primers, and in biological assays.

Where the polynucleotides are used to assess carboxypeptidase properties or functions, such as in the assays described herein, all or less than all of the entire cDNA can be useful. Assays specifically directed to carboxypeptidase functions, such as assessing agonist or antagonist activity, encompass the use of known fragments. Further, diagnostic methods for assessing carboxypeptidase function can also be practiced with any fragment, including those fragments that may have been known prior to the invention. Similarly, in methods involving treatment of carboxypeptidase dysfunction, all fragments are encompassed including those, which may have been known in the art.

The carboxypeptidase polynucleotides are useful as a hybridization probe for cDNA and genomic DNA to isolate a full-length cDNA and genomic clones encoding the polypeptides described in SEQ ID NO 1 and to isolate cDNA and genomic clones that correspond to variants producing the same polypeptides shown in SEQ ID NO 1 or the other variants described herein. Variants can be isolated from the same tissue and organism from which the polypeptides shown in SEQ ID NO 1 were isolated, different tissues from the same organism, or from different organisms. This method is useful for isolating genes and cDNA that are developmentally-controlled and therefore may be expressed in the same tissue or different tissues at different points in the development of an organism.

The probe can correspond to any sequence along the entire length of the gene encoding the carboxypeptidase. Accordingly, it could be derived from 5' noncoding regions, the coding region, and 3' noncoding regions.

The nucleic acid probe can be, for example, the full-length cDNA of SEQ ID NO 2, or a fragment thereof, such as an oligonucleotide of at least 12, 15, 30, 50, 100, 250 or 500 nucleotides in length and sufficient to specifically hybridize under stringent conditions to mRNA or DNA.

Fragments of the polynucleotides described herein are also useful to synthesize larger fragments or full-length polynucleotides described herein. For example, a fragment can be hybridized to any portion of an mRNA and a larger or full-length cDNA can be produced.

The fragments are also useful to synthesize antisense molecules of desired length and sequence.

Antisense nucleic acids of the invention can be designed using the nucleotide sequences of SEQ ID NO 2, and constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670. PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res.* 24(17):3357–63, Mag et al. (1989) *Nucleic Acids Res.* 17:5973, and Peterser et al. (1975) *Bioorganic Med. Chem. Lett.* 5:1119.

The nucleic acid molecules and fragments of the invention can also include other appended groups such as peptides (e.g., for targeting host cell carboxypeptidases in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/0918) or the blood brain barrier (see, e.g., PCT Publication No. WO 89/10134). In addition, oligonucleotides can be modified with hybridization-triggered cleavage agents (see, e.g., Krol et al. (1988) *Bio-Techniques* 6:958–976) or intercalating agents (see, e.g., Zon (1988) *Pharm Res.* 5:539–549).

The carboxypeptidase polynucleotides are also useful as primers for PCR to amplify any given region of a carboxypeptidase polynucleotide.

The carboxypeptidase polynucleotides are also useful for constructing recombinant vectors. Such vectors include expression vectors that express a portion of, or all of, the carboxypeptidase polypeptides. Vectors also include insertion vectors, used to integrate into another polynucleotide sequence, such as into the cellular genome, to alter in situ expression of carboxypeptidase genes and gene products. For example, an endogenous carboxypeptidase coding sequence can be replaced via homologous recombination with all or part of the coding region containing one or more specifically introduced mutations.

The carboxypeptidase polynucleotides are also useful for expressing antigenic portions of the carboxypeptidase proteins.

The carboxypeptidase polynucleotides are also useful as probes for determining the chromosomal positions of the carboxypeptidase polynucleotides by means of in situ hybridization methods, such as FISH. (For a review of this technique, see Verma et al. (1988) *Human Chromosomes: A Manual of Basic Techniques* (Pergamon Press, New York), and PCR mapping of somatic cell hybrids. The mapping of the sequences to chromosomes is an important first step in correlating these sequences with genes associated with disease.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between a gene and a disease mapped to the same chromosomal region, can then be identified through linkage analysis (co-inheritance of physically adjacent genes), described in, for example, Egeland et al. ((1987) *Nature* 325:783–787).

Moreover, differences in the DNA sequences between individuals affected with or free of a disease associated with a specified gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations, that are visible from chromosome spreads, or detectable using PCR based on that DNA sequence. Ultimately, complete sequencing of genes from several individuals can be performed to confirm the presence of a mutation and to distinguish mutations from polymorphisms.

The carboxypeptidase polynucleotide probes are also useful to determine patterns of the presence of the gene encoding the carboxypeptidases and their variants with respect to tissue distribution, for example, whether gene duplication has occurred and whether the duplication occurs in all or only a subset of tissues. The genes can be naturally occurring or can have been introduced into a cell, tissue, or organism exogenously.

The carboxypeptidase polynucleotides are also useful for designing ribozymes corresponding to all, or a part, of the mRNA produced from genes encoding the polynucleotides described herein.

The carboxypeptidase polynucleotides are also useful for constructing host cells expressing a part, or all, of the carboxypeptidase polynucleotides and polypeptides.

The carboxypeptidase polynucleotides are also useful for constructing transgenic animals expressing all, or a part, of the carboxypeptidase polynucleotides and polypeptides.

The carboxypeptidase polynucleotides are also useful for making vectors that express part, or all, of the carboxypeptidase polypeptides.

The carboxypeptidase polynucleotides are also useful as hybridization probes for determining the level of carboxypeptidase nucleic acid expression. Accordingly, the probes can be used to detect the presence of, or to determine levels of, carboxypeptidase nucleic acid in cells, tissues, and in organisms. The nucleic acid whose level is determined can be DNA or RNA. Accordingly, probes corresponding to the polypeptides described herein can be used to assess gene copy number in a given cell, tissue, or organism. This is particularly relevant in cases in which there has been an amplification of the carboxypeptidase genes.

Alternatively, the probe can be used in an in situ hybridization context to assess the position of extra copies of the carboxypeptidase genes, as on extrachromosomal elements or as integrated into chromosomes in which the carboxypeptidase gene is not normally found, for example as a homogeneously staining region.

These uses are relevant for diagnosis of disorders involving an increase or decrease in carboxypeptidase expression relative to normal, such as a proliferative disorder, a differentiative or developmental disorder, or a hematopoietic disorder.

Disorders in which the carboxypeptidase expression is relevant include, but are not limited to, breast, colon and lung carcinoma, and to disorders involving the tissues in which the gene is expressed, especially as disclosed herein.

Thus, the present invention provides a method for identifying a disease or disorder associated with aberrant expression or activity of carboxypeptidase nucleic acid, in which a test sample is obtained from a subject and nucleic acid (e.g., mRNA, genomic DNA) is detected, wherein the presence of the nucleic acid is diagnostic for a subject having or at risk of developing a disease or disorder associated with aberrant expression or activity of the nucleic acid.

One aspect of the invention relates to diagnostic assays for determining nucleic acid expression as well as activity in the context of a biological sample (e.g., blood, serum, cells, tissue) to determine whether an individual has a disease or disorder, or is at risk of developing a disease or disorder, associated with aberrant nucleic acid expression or activity. Such assays can be used for prognostic or predictive purpose to thereby prophylactically treat an individual prior to the onset of a disorder characterized by or associated with expression or activity of the nucleic acid molecules.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express the carboxypeptidase, such as by measuring the level of a carboxypeptidase-coding nucleic acid in a sample of cells from a subject e.g., mRNA or genomic DNA, or determining if the carboxypeptidase gene has been mutated.

Nucleic acid expression assays are useful for drug screening to identify compounds that modulate carboxypeptidase nucleic acid expression (e.g., antisense, polypeptides, peptidomimetics, small molecules or other drugs). A cell is contacted with a candidate compound and the expression of mRNA determined. The level of expression of the mRNA in the presence of the candidate compound is compared to the level of expression of the mRNA in the absence of the candidate compound. The candidate compound can then be identified as a modulator of nucleic acid expression based on this comparison and be used, for example to treat a disorder characterized by aberrant nucleic acid expression. The modulator can bind to the nucleic acid or indirectly modulate expression, such as by interacting with other cellular components that affect nucleic acid expression Modulatory methods can be performed in vitro (e.g., by culturing the cell with the agent) or, alternatively, in vivo (e.g., by administering the gent to a subject) in patients or in transgenic animals.

The invention thus provides a method for identifying a compound that can be used to treat a disorder associated with nucleic acid expression of the carboxypeptidase gene. The method typically includes assaying the ability of the compound to modulate the expression of the carboxypeptidase nucleic acid and thus identifying a compound that can be used to treat a disorder characterized by undesired carboxypeptidase nucleic acid expression.

The assays can be performed in cell-based and cell-free systems. Cell-based assays include cells naturally expressing the carboxypeptidase nucleic acid or recombinant cells genetically engineered to express specific nucleic acid sequences.

Alternatively, candidate compounds can be assayed in vivo in patients or in transgenic animals.

The assay for carboxypeptidase nucleic acid expression can involve direct assay of nucleic acid levels, such as mRNA levels, or on collateral compounds involved in the pathway. Further, the expression of genes that are up- or down-regulated in response to the carboxypeptidase pathway can also be assayed. In this embodiment the regulatory regions of these genes can be operably linked to a reporter gene such as luciferase.

Thus, modulators of carboxypeptidase gene expression can be identified in a method wherein a cell is contacted with a candidate compound and the expression of mRNA determined. The level of expression of carboxypeptidase mRNA in the presence of the candidate compound is compared to the level of expression of carboxypeptidase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

Accordingly, the invention provides methods of treatment, with the nucleic acid as a target, using a compound identified through drug screening as a gene modulator to modulate carboxypeptidase nucleic acid expression. Modulation includes both up-regulation (i.e. activation or agonization) or down-regulation (suppression or antagonization) or effects on nucleic acid activity (e.g. when nucleic acid is mutated or improperly modified). Treatment is of disorders characterized by aberrant expression or activity of the nucleic acid.

Disorders in which the carboxypeptidase expression is relevant include, but are not limited to, breast, colon and lung carcinoma, and to disorders involving the tissues in which the gene is expressed, especially as disclosed herein.

Alternatively, a modulator for carboxypeptidase nucleic acid expression can be a small molecule or drug identified using the screening assays described herein as long as the drug or small molecule inhibits the carboxypeptidase nucleic acid expression.

The carboxypeptidase polynucleotides are also useful for monitoring the effectiveness of modulating compounds on the expression or activity of the carboxypeptidase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

Monitoring can be, for example, as follows: (i) obtaining a pre-administration sample from a subject prior to administration of the agent; (ii) detecting the level of expression of a specified mRNA or genomic DNA of the invention in the pre-administration sample; (iii) obtaining one or more post-administration samples from the subject; (iv) detecting the level of expression or activity of the mRNA or genomic DNA in the post-administration samples; (v) comparing the level of expression or activity of the mRNA or genomic DNA in the pre-administration sample with the mRNA or genomic DNA in the post-administration sample or samples; and (vi) increasing or decreasing the administration of the agent to the subject accordingly.

The carboxypeptidase polynucleotides are also useful in diagnostic assays for qualitative changes in carboxypeptidase nucleic acid, and particularly in qualitative changes that lead to pathology. The polynucleotides can be used to detect mutations in carboxypeptidase genes and gene expression products such as mRNA. The polynucleotides can be used as hybridization probes to detect naturally-occurring genetic mutations in the carboxypeptidase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the carboxypeptidase gene associated with a dysfunction provides a diagnostic tool for an active disease or susceptibility to disease when the disease results from overexpression, underexpression, or altered expression of a carboxypeptidase.

Mutations in the carboxypeptidase gene can be detected at the nucleic acid level by a variety of techniques. Genomic DNA can be analyzed directly or can be amplified by using PCR prior to analysis. RNA or cDNA can be used in the same way.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

Alternatively, mutations in a carboxypeptidase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozymne cleavage site.

Perfectly matched sequences can be distinguished from mismatched sequences by nuclease cleavage digestion assays or by differences in melting temperature. Sequence changes at specific locations can also be assessed by nuclease protection assays such as RNase and S1 protection or the chemical cleavage method. Furthermore, sequence differences between a mutant carboxypeptidase gene and a wild-type gene can be determined by direct DNA sequencing. A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 21 7:286–295), electrophoretic mobility of mutant and wild type nucleic acid is compared (Orita et al. (1989) *PNAS* 86:2766; Cotton et al. (1993) *Mutat. Res.* 285:125–144; and Hayashi et al. (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al. (1985) *Nature* 313:495). The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet.* 7:5). Examples of other techniques for detecting point mutations include, selective oligonucleotide hybridization, selective amplification, and selective primer extension.

In other embodiments, genetic mutations can be identified by hybridizing a sample and control nucleic acids, e.g., DNA or RNA, to high density arrays containing hundreds or thousands of oligonucleotide probes (Cronin et al. (1996) *Human Mutation* 7:244–255; Kozal et al. (1996) *Nature Medicine* 2:753–759). For example, genetic mutations can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

The carboxypeptidase polynucleotides are also useful for testing an individual for a genotype that while not necessarily causing the disease, nevertheless affects the treatment modality. Thus, the polynucleotides can be used to study the relationship between an individual's genotype and the individual's response to a compound used for treatment (pharmacogenomic relationship). In the present case, for example, a mutation in the carboxypeptidase gene that results in altered affinity for substrate could result in an excessive or decreased drug effect with standard concentrations of substrate. Accordingly, the carboxypeptidase polynucleotides described herein can be used to assess the mutation content of the gene in an individual in order to select an appropriate compound or dosage regimen for treatment.

Thus polynucleotides displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The methods can involve obtaining a control biological sample from a control subject, contacting the control sample with a compound or agent capable of detecting mRNA, or genomic DNA, such that the presence of mRNA or genomic DNA is detected in the biological sample, and comparing the presence of mRNA or genomic DNA in the control sample with the presence of mRNA or genomic DNA in the test sample.

The carboxypeptidase polynucleotides are also useful for chromosome identification when the sequence is identified with an individual chromosome and to a particular location on the chromosome. First, the DNA sequence is matched to the chromosome by in situ or other chromosome-specific hybridization. Sequences can also be correlated to specific chromosomes by preparing PCR primers that can be used for PCR screening of somatic cell hybrids containing individual chromosomes from the desired species. Only hybrids containing the chromosome containing the gene homologous to the primer will yield an amplified fragment. Sublocalization can be achieved using chromosomal fragments. Other strategies include prescreening with labeled flow-sorted chromosomes and preselection by hybridization to chromosome-specific libraries. Further mapping strategies include fluorescence in situ hybridization, which allows hybridization with probes shorter than those traditionally used. Reagents for chromosome mapping can be used individually to mark a single chromosome or a single site on the chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

The carboxypeptidase polynucleotides can also be used to identify individuals from small biological samples. This can be done for example using restriction fragment-length polymorphism (RFLP) to identify an individual. Thus, the polynucleotides described herein are useful as DNA markers for RFLP (See U.S. Pat. No. 5,272,057).

Furthermore, the carboxypeptidase sequence can be used to provide an alternative technique, which determines the actual DNA sequence of selected fragments in the genome of an individual. Thus, the carboxypeptidase sequences described herein can be used to prepare two PCR primers from the 5' and 3' ends of the sequences. These primers can then be used to amplify DNA from an individual for subsequent sequencing.

Panels of corresponding DNA sequences from individuals prepared in this manner can provide unique individual identifications, as each individual will have a unique set of such DNA sequences. It is estimated that allelic variation in humans occurs with a frequency of about once per each 500 bases. Allelic variation occurs to some degree in the coding regions of these sequences, and to a greater degree in the noncoding regions. The carboxypeptidase sequences can be used to obtain such identification sequences from individuals and from tissue. The sequences represent unique fragments of the human genome. Each of the sequences described herein can, to some degree, be used as a standard against which DNA from an individual can be compared for identification purposes.

If a panel of reagents from the sequences is used to generate a unique identification database for an individual, those same reagents can later be used to identify tissue from that individual. Using the unique identification database, positive identification of the individual, living or dead, can be made from extremely small tissue samples.

The carboxypeptidase polynucleotides can also be used in forensic identification procedures. PCR technology can be used to amplify DNA sequences taken from very small biological samples, such as a single hair follicle, body fluids (e.g. blood, saliva, or semen). The amplified sequence can then be compared to a standard allowing identification of the origin of the sample.

The carboxypeptidase polynucleotides can thus be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region are particularly useful since greater polymorphism occurs in the noncoding regions, making it easier to differentiate individuals using this technique.

The carboxypeptidase polynucleotides can further be used to provide polynucleotide reagents, e.g., labeled or labelable probes which can be used in, for example, an in situ hybridization technique, to identify a specific tissue. This is useful in cases in which a forensic pathologist is presented with a tissue of unknown origin. Panels of carboxypeptidase probes can be used to identify tissue by species and/or by organ type.

In a similar fashion, these primers and probes can be used to screen tissue culture for contamination (i.e. screen for the presence of a mixture of different types of cells in a culture).

Alternatively, the carboxypeptidase polynucleotides can be used directly to block transcription or translation of carboxypeptidase gene sequences by means of antisense or ribozyme constructs. Thus, in a disorder characterized by abnormally high or undesirable carboxypeptidase gene expression, nucleic acids can be directly used for treatment.

The carboxypeptidase polynucleotides are thus useful as antisense constructs to control carboxypeptidase gene expression in cells, tissues, and organisms. A DNA antisense polynucleotide is designed to be complementary to a region of the gene involved in transcription, preventing transcription and hence production of carboxypeptidase protein. An antisense RNA or DNA polynucleotide would hybridize to the mRNA and thus block translation of mRNA into carboxypeptidase protein.

Examples of antisense molecules useful to inhibit nucleic acid expression include antisense molecules complementary to a fragment of the 5' untranslated region of SEQ ID NO 2 which also includes the start codon and antisense molecules which are complementary to a fragment of the 3' untranslated region of SEQ ID NO 2.

Alternatively, a class of antisense molecules can be used to inactivate mRNA in order to decrease expression of carboxypeptidase nucleic acid. Accordingly, these molecules can treat a disorder characterized by abnormal or undesired carboxypeptidase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the carboxypeptidase protein.

The carboxypeptidase polynucleotides also provide vectors for gene therapy in patients containing cells that are aberrant in carboxypeptidase gene expression. Thus, recombinant cells, which include the patient's cells that have been engineered ex vivo and returned to the patient, are introduced into an individual where the cells produce the desired carboxypeptidase protein to treat the individual.

The invention also encompasses kits for detecting the presence of a carboxypeptidase nucleic acid in a biological sample. For example, the kit can comprise reagents such as a labeled or labelable nucleic acid or agent capable of detecting carboxypeptidase nucleic acid in a biological sample; means for determining the amount of carboxypeptidase nucleic acid in the sample; and means for comparing the amount of carboxypeptidase nucleic acid in the sample with a standard. The compound or agent can be packaged in a suitable container. The kit can further comprise instructions for using the kit to detect carboxypeptidase mRNA or DNA.

Computer Readable Means

The nucleotide or amino acid sequences of the invention are also provided in a variety of mediums to facilitate use thereof. As used herein, "provided" refers to a manufacture, other than an isolated nucleic acid or amino acid molecule, which contains a nucleotide or amino acid sequence of the present invention. Such a manufacture provides the nucleotide or amino acid sequences, or a subset thereof (e.g., a subset of open reading frames (ORFs)) in a form which allows a skilled artisan to examine the manufacture using means not directly applicable to examining the nucleotide or amino acid sequences, or a subset thereof, as they exists in nature or in purified form.

In one application of this embodiment, a nucleotide or amino acid sequence of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a nucleotide or amino acid sequence of the present invention.

As used herein, "recorded" refers to a process for storing information on computer readable medium. The skilled artisan can readily adopt any of the presently known methods for recording information on computer readable medium to generate manufactures comprising the nucleotide or amino acid sequence information of the present invention.

A variety of data storage structures are available to a skilled artisan for creating a computer readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of dataprocessor structuring formats (e.g., text file or database) in order to obtain computer readable medium having recorded thereon the nucleotide sequence information of the present invention.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTX (NCBIA).

For example, software which implements the BLAST (Altschul et al. (1990) *J. Mol. Biol.* 215:403–410) and BLAZE (Brutlag et al. (1993) *Comp. Chem.* 17:203–207) search algorithms on a Sybase system can be used to identify open reading frames (ORFs) of the sequences of the invention which contain homology to ORFs or proteins from other libraries. Such ORFs are protein encoding fragments and are useful in producing commercially important proteins such as enzymes used in various reactions and in the production of commercially useful metabolites.

Vectors/Host Cells

The invention also provides vectors containing the carboxypeptidase polynucleotides. The term "vector" refers to a vehicle, preferably a nucleic acid molecule that can transport the carboxypeptidase polynucleotides. When the vector is a nucleic acid molecule, the carboxypeptidase polynucleotides are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the carboxypeptidase polynucleotides. Alternatively, the vector may integrate into the host cell genome and produce additional copies of the carboxypeptidase polynucleotides when the host cell replicates.

The invention provides vectors for the maintenance (cloning vectors) or vectors for expression (expression vectors) of the carboxypeptidase polynucleotides. The vectors can function in procaryotic or eukaryotic cells or in both (shuttle vectors).

Expression vectors contain cis-acting regulatory regions that are operably linked in the vector to the carboxypeptidase polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the carboxypeptidase polynucleotides from the vector. Alternatively, a trans-acting factor may be supplied by the host cell. Finally, a trans-acting factor can be produced from the vector itself.

It is understood, however, that in some embodiments, transcription and/or translation of the carboxypeptidase polynucleotides can occur in a cell-free system.

The regulatory sequence to which the polynucleotides described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al. (1989) *Molecular Cloning: A Laboratory Manual 2nd. ed.*, Cold Spring Harbor Laboratory Press, Cold Spring Harbor, N.Y.).

A variety of expression vectors can be used to express a carboxypeptidase polynucleotide. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al. (1989) *Molecular Cloning: A Laboratory Manual 2nd. ed.*, Cold Spring Harbor Laboratory Press, Cold Spring Harbor, N.Y.

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The carboxypeptidase polynucleotides can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate polynucleotide can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the polypeptide as a fusion protein. Accordingly, the invention provides fusion vectors that allow for the production of the carboxypeptidase polypeptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired polypeptide can ultimately be separated from the fusion moiety. Proteolytic enzymes include, but are not limited to, factor Xa, thrombin, and enterokinase. Typical fusion expression vectors include pGEX (Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al. (1988) *Gene* 69:301–315) and pET 11d (Studier et al. (1990) *Gene Expression Technology: Methods in Enzymology* 185:60–89).

Recombinant protein expression can be maximized in a host bacteria by providing a genetic background wherein the host cell has an impaired capacity to proteolytically cleave the recombinant protein. (Gottesman, S. (1990) *Gene Expression Technology: Methods in Enzymology* 185, Academic Press, San Diego, Calif. 119–128). Alternatively, the sequence of the polynucleotide of interest can be altered to provide preferential codon usage for a specific host cell, for example *E. coli*. (Wada et al. (1992) *Nucleic Acids Res.* 20:2111–2118).

The carboxypeptidase polynucleotides can also be expressed by expression vectors that are operative in yeast. Examples of vectors for expression in yeast e.g., *S. cerevisiae* include pYepSec1 (Baldari et al. (1987) *EMBO J.* 6:229–234 ), pMFa (Kurjan et al. (1982) *Cell* 30:933–943), pJRY88 (Schultz et al. (1987) *Gene* 54:113–123), and pYES2 (Invitrogen Corporation, San Diego, Calif.).

The carboxypeptidase polynucleotides can also be expressed in insect cells using, for example, baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow et al. (1989) *Virology* 170:31–39).

In certain embodiments of the invention, the polynucleotides described herein are expressed in mammalian cells using mammalian expression vectors. Examples of mammalian expression vectors include pCDM8 (Seed, B. (1987) *Nature* 329:840) and pMT2PC (Kaufinan et al. (1987) *EMBO J.* 6:187–195).

The expression vectors listed herein are provided by way of example only of the well-known vectors available to those of ordinary skill in the art that would be useful to express the carboxypeptidase polynucleotides. The person of ordinary skill in the art would be aware of other vectors suitable for maintenance propagation or expression of the polynucleotides described herein. These are found for example in Sambrook et al. (1989) *Molecular Cloning: A Laboratory Manual* 2nd, ed., Cold Spring Harbor Laboratory, Cold Spring Harbor Laboratory Press, Cold Spring Harbor, N.Y.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook et al. (*Molecular Cloning: A Laboratory Manual*, 2d ed., Cold Spring Harbor Laboratory, Cold Spring Harbor Laboratory Press, Cold Spring Harbor, N.Y.).

Host cells can contain more than one vector. Thus, different nucleotide sequences can be introduced on different vectors of the same cell. Similarly, the carboxypeptidase polynucleotides can be introduced either alone or with other polynucleotides that are not related to the carboxypeptidase polynucleotides such as those providing trans-acting factors for expression vectors. When more than one vector is introduced into a cell, the vectors can be introduced independently, co-introduced or joined to the carboxypeptidase polynucleotide vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the polynucleotides described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the polypeptide is desired, appropriate secretion signals are incorporated into the vector. The signal sequence can be endogenous to the carboxypeptidase polypeptides or heterologous to these polypeptides. Where the polypeptide is not secreted into the medium, the protein can be isolated from the host cell by standard disruption procedures, including freeze thaw, sonication, mechanical disruption, use of lysing agents and the like. The polypeptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the polypeptides described herein, the polypeptides can have various glycosylation patterns, depending upon the cell, or maybe non-glycosylated as when produced in bacteria. In addition, the polypeptides may include an initial modified methionine in some cases as a result of a host-mediated process.

Uses of Vectors and Host Cells

It is understood that "host cells" and "recombinant host cells" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The host cells expressing the polypeptides described herein, and particularly recombinant host cells, have a variety of uses. First, the cells are useful for producing carboxypeptidase proteins or polypeptides that can be further purified to produce desired amounts of carboxypeptidase protein or fragments. Thus, host cells containing expression vectors are useful for polypeptide production.

Host cells are also useful for conducting cell-based assays involving the carboxypeptidase or carboxypeptidase fragments. Thus, a recombinant host cell expressing a native carboxypeptidase is useful to assay for compounds that stimulate or inhibit carboxypeptidase function.

Host cells are also useful for identifying carboxypeptidase mutants in which these functions are affected. If the mutants naturally occur and give rise to a pathology, host cells containing the mutations are useful to assay compounds that have a desired effect on the mutant carboxypeptidase (for example, stimulating or inhibiting function) which may not be indicated by their effect on the native carboxypeptidase.

Recombinant host cells are also useful for expressing the chimeric polypeptides described herein to assess compounds that activate or suppress activation by means of a heterologous domain, segment, site, and the like, as disclosed herein.

Further, mutant carboxypeptidases can be designed in which one or more of the various functions is engineered to be increased or decreased (e.g., peptide substrate binding) and used to augment or replace carboxypeptidase proteins in an individual. Thus, host cells can provide a therapeutic benefit by replacing an aberrant carboxypeptidase or providing an aberrant carboxypeptidase that provides a therapeutic result. In one embodiment, the cells provide carboxypeptidases that are abnormally active.

In another embodiment, the cells provide carboxypeptidases that are abnormally inactive. These carboxypeptidases can compete with endogenous carboxypeptidases in the individual.

In another embodiment, cells expressing carboxypeptidases that cannot be activated, are introduced into an individual in order to compete with endogenous carboxypeptidases for substrate. For example, in the case in which excessive substrate is part of a treatment modality, it may be necessary to inactivate this molecule at a specific point in treatment. Providing cells that compete for the molecule, but which cannot be affected by carboxypeptidase activation would be beneficial.

Homologously recombinant host cells can also be produced that allow the in situ alteration of endogenous carboxypeptidase polynucleotide sequences in a host cell genome. This technology is more fully described in WO 93/09222, WO 91/12650 and U.S. Pat. No. 5,641,670. Briefly, specific polynucleotide sequences corresponding to the carboxypeptidase polynucleotides or sequences proximal or distal to a carboxypeptidase gene are allowed to integrate into a host cell genome by homologous recombination where expression of the gene can be affected. In one embodiment, regulatory sequences are introduced that either increase or decrease expression of an endogenous sequence. Accordingly, a carboxypeptidase protein can be produced in a cell not normally producing it, or increased expression of carboxypeptidase protein can result in a cell normally producing the protein at a specific level. Alternatively, the entire gene can be deleted. Still further, specific mutations can be introduced into any desired region of the gene to produce mutant carboxypeptidase proteins. Such mutations could be introduced, for example, into the specific regions disclosed herein.

In one embodiment, the host cell can be a fertilized oocyte or embryonic stem cell that can be used to produce a transgenic animal containing the altered carboxypeptidase gene. Alternatively, the host cell can be a stem cell or other early tissue precursor that gives rise to a specific subset of cells and can be used to produce transgenic tissues in an animal. See also Thomas et al., Cell 51:503 (1987) for a description of homologous recombination vectors. The vector is introduced into an embryonic stem cell line (e.g., by electroporation) and cells in which the introduced gene has homologously recombined with the endogenous carboxypeptidase gene is selected (see e.g., Li, E. et al. (1992) Cell 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; and WO 93/04169.

The genetically engineered host cells can be used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a carboxypeptidase protein and identifying and evaluating modulators of carboxypeptidase protein activity.

Other examples of transgenic animals include non-human primates, sheep, dogs, cows, goats, chickens, and amphibians.

In one embodiment, a host cell is a fertilized oocyte or an embryonic stem cell into which carboxypeptidase polynucleotide sequences have been introduced.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the carboxypeptidase nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the carboxypeptidase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems, which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *S. cerevisiae* (O'Gorman et al. (1991) *Science* 251:1351–1355. If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to a pseudopregnant female foster animal. The offspring born of this female foster animal will be a clone of the animal from which the cell, e.g., the somatic cell, is isolated.

Transgenic animals containing recombinant cells that express the polypeptides described herein are useful to conduct the assays described herein in an in vivo context. Accordingly, the various physiological factors that are present in vivo and that could affect, for example, substrate binding and hydrolysis or carboxypeptidase activation, may not be evident from in vitro cell-free or cell-based assays. Accordingly, it is useful to provide non-human transgenic animals to assay in vivo carboxypeptidase function, including substrate interaction, the effect of specific mutant carboxypeptidases on carboxypeptidase function and substrate interaction, and the effect of chimeric carboxypeptidases. It is also possible to assess the effect of null mutations, that is mutations that substantially or completely eliminate one or more carboxypeptidase functions.

Pharmaceutical Compositions

The carboxypeptidase nucleic acid molecules, protein, modulators of the protein, and antibodies (also referred to herein as "active compounds") can be incorporated into pharmaceutical compositions suitable for administration to a subject, e.g., a human. Such compositions typically comprise the nucleic acid molecule, protein, modulator, or antibody and a pharmaceutically acceptable carrier.

The term "administer" is used in its broadest sense and includes any method of introducing the compositions of the present invention into a subject. This includes producing polypeptides or polynucleotides in vivo as by transcription or translation in vivo of polynucleotides that have been exogenously introduced into a subject. Thus, polypeptides or nucleic acids produced in the subject from the exogenous compositions are encompassed in the term "administer."

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a carboxypeptidase protein or anti-carboxypeptidase antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

This invention may be embodied in many different forms and should not be construed as limited to the embodiments set forth herein; rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

What is claimed is:

1. An isolated nucleic acid molecule comprising a nucleotide sequence selected from the group consisting of:

(a) the nucleotide sequence shown in SEQ ID NO: 2;

(b) a nucleotide sequence which encodes a polypeptide comprising the amino acid sequence of SEQ ID NO:1;

(c) the cDNA insert of the plasmid deposited with ATCC Patent Deposit No. PTA-1643;

(d) a nucleotide sequence that encodes a polypeptide encoded by the cDNA insert of the plasmid deposited with ATCC Patent Deposit No. PTA-1643; and (e) a nucleotide sequence that is fully complementary to a nucleotide sequence of (a), (b), (c), or (d).

2. Any one of the nucleic acid molecules of claim 1 further comprising vector nucleic acid sequences.

3. Any one of the nucleic acid molecules of claim 1 further comprising nucleic acid sequences encoding a heterologous polypeptide.

4. A host cell engineered to express any one of the nucleic acid molecules of claim 1.

5. A method for producing a polypeptide encoded by any of the nucleotide sequences of claim 1.

* * * * *

UNITED STATES PATENT AND TRADEMARK OFFICE
CERTIFICATE OF CORRECTION

PATENT NO. : 6,369,210 B1 Page 1 of 1
DATED : April 9, 2002
INVENTOR(S) : Kapeller-Libermann et al.

It is certified that error appears in the above-identified patent and that said Letters Patent is hereby corrected as shown below:

<u>Title page,</u>
Item [56], References Cited, OTHER PUBLICATIONS,
"A1678665" should read -- AI678665 -- (both occurances).

<u>Column 6,</u>
Lines 1-2, the period (.) after "fam-ily" should be relocated to the end of the sentence after "(SEQ ID NO:4)."
Lines 1-2, "AND AN ALPHA/BETA HYDROLASE" should be in lower case;
Line 13, after "pattern" insert -- of SEQ ID NO:1 --;
Line 14, cancel "SEQ ID NO:1".

Signed and Sealed this

Twelfth Day of November, 2002

*Attest:*

JAMES E. ROGAN
*Attesting Officer*  *Director of the United States Patent and Trademark Office*

SEQUENCE LISTING

<160> NUMBER OF SEQ ID NOS: 4

<210> SEQ ID NO 1
<211> LENGTH: 492
<212> TYPE: PRT
<213> ORGANISM: Homo sapiens

<400> SEQUENCE: 1

```
Met Gly Ser Ala Pro Trp Ala Pro Val Leu Leu Leu Ala Leu Gly Leu
 1               5                  10                  15

Arg Gly Leu Gln Ala Gly Ala Arg Arg Ala Pro Asp Pro Gly Phe Gln
            20                  25                  30

Glu Arg Phe Phe Gln Gln Arg Leu Asp His Phe Asn Phe Glu Arg Phe
        35                  40                  45

Gly Asn Lys Thr Phe Pro Gln Arg Phe Leu Val Ser Asp Arg Phe Trp
    50                  55                  60

Val Arg Gly Glu Gly Pro Ile Phe Phe Tyr Thr Gly Asn Glu Gly Asp
65                  70                  75                  80

Val Trp Ala Phe Ala Asn Asn Ser Gly Phe Val Ala Glu Leu Ala Ala
                85                  90                  95

Glu Arg Gly Ala Leu Leu Val Phe Ala Glu His Arg Tyr Tyr Gly Lys
            100                 105                 110
```

```
Ser Leu Pro Phe Gly Ala Gln Ser Thr Gln Arg Gly His Thr Glu Leu
        115                 120                 125

Leu Thr Val Glu Gln Ala Leu Ala Asp Phe Ala Glu Leu Leu Arg Ala
130                 135                 140

Leu Arg Arg Asp Leu Gly Ala Gln Asp Ala Pro Ala Ile Ala Phe Gly
145                 150                 155                 160

Gly Ser Tyr Gly Gly Met Leu Ser Ala Tyr Leu Arg Met Lys Tyr Pro
                165                 170                 175

His Leu Val Ala Gly Ala Leu Ala Ser Ala Pro Val Leu Ala Val
            180                 185                 190

Ala Gly Leu Gly Asp Ser Asn Gln Phe Phe Arg Asp Val Thr Ala Asp
        195                 200                 205

Phe Glu Gly Gln Ser Pro Lys Cys Thr Gln Gly Val Arg Glu Ala Phe
210                 215                 220

Arg Gln Ile Lys Asp Leu Phe Leu Gln Gly Ala Tyr Asp Thr Val Arg
225                 230                 235                 240

Trp Glu Phe Gly Thr Cys Gln Pro Leu Ser Asp Glu Lys Asp Leu Thr
                245                 250                 255

Gln Leu Phe Met Phe Ala Arg Asn Ala Phe Thr Val Leu Ala Met Met
            260                 265                 270

Asp Tyr Pro Tyr Pro Thr Asp Phe Leu Gly Pro Leu Pro Ala Asn Pro
        275                 280                 285

Val Lys Val Gly Cys Asp Arg Leu Leu Ser Glu Ala Gln Arg Ile Thr
290                 295                 300

Gly Leu Arg Ala Leu Ala Gly Leu Val Tyr Asn Ala Ser Gly Ser Glu
305                 310                 315                 320

His Cys Tyr Asp Ile Tyr Arg Leu Tyr His Ser Cys Ala Asp Pro Thr
                325                 330                 335

Gly Cys Gly Thr Gly Pro Asp Ala Arg Ala Trp Asp Tyr Gln Ala Cys
            340                 345                 350

Thr Glu Ile Asn Leu Thr Phe Ala Ser Asn Asn Val Thr Asp Met Phe
        355                 360                 365

Pro Asp Leu Pro Phe Thr Asp Glu Leu Arg Gln Arg Tyr Cys Leu Asp
370                 375                 380

Thr Trp Gly Val Trp Pro Arg Pro Asp Trp Leu Leu Thr Ser Phe Trp
385                 390                 395                 400

Gly Gly Asp Leu Arg Ala Ala Ser Asn Ile Ile Phe Ser Asn Gly Asn
                405                 410                 415

Leu Asp Pro Trp Ala Gly Gly Ile Arg Arg Asn Leu Ser Ala Ser
            420                 425                 430

Val Ile Ala Val Thr Ile Gln Gly Gly Ala His His Leu Asp Leu Arg
435                 440                 445

Ala Ser His Pro Glu Asp Pro Ala Ser Val Val Glu Ala Arg Lys Leu
450                 455                 460

Glu Ala Thr Ile Ile Gly Glu Trp Val Lys Ala Ala Arg Arg Glu Gln
465                 470                 475                 480

Gln Pro Ala Leu Arg Gly Gly Pro Arg Leu Ser Leu
                485                 490

<210> SEQ ID NO 2
<211> LENGTH: 1653
<212> TYPE: DNA
<213> ORGANISM: Homo sapiens
<220> FEATURE:
<221> NAME/KEY: CDS
```

<222> LOCATION: (19)...(1494)

<400> SEQUENCE: 2

| | | |
|---|---|---|
| cgtccggcgg aaggcgac atg ggc tcc gct ccc tgg gcc ccg gtc ctg ctg<br>                            Met Gly Ser Ala Pro Trp Ala Pro Val Leu Leu<br>                             1                5                       10 | 51 |
| ctg gcg ctc ggg ctg cgc ggc ctc cag gcg ggg gcc cgc agg gcc ccg<br>Leu Ala Leu Gly Leu Arg Gly Leu Gln Ala Gly Ala Arg Arg Ala Pro<br>             15                    20                   25 | 99 |
| gac ccc ggc ttc cag gag cgc ttc ttc cag cag cgt ctg gac cac ttc<br>Asp Pro Gly Phe Gln Glu Arg Phe Phe Gln Gln Arg Leu Asp His Phe<br>    30                    35                    40 | 147 |
| aac ttc gag cgc ttc ggc aac aag acc ttc cct cag cgc ttc ctg gtg<br>Asn Phe Glu Arg Phe Gly Asn Lys Thr Phe Pro Gln Arg Phe Leu Val<br>45                    50                    55 | 195 |
| tcg gac agg ttc tgg gtc cgg ggc gag ggg ccc atc ttc ttc tac act<br>Ser Asp Arg Phe Trp Val Arg Gly Glu Gly Pro Ile Phe Phe Tyr Thr<br>60                    65                    70                   75 | 243 |
| ggg aac gag ggc gac gtg tgg gcc ttc gcc aac aac tcg ggc ttc gtc<br>Gly Asn Glu Gly Asp Val Trp Ala Phe Ala Asn Asn Ser Gly Phe Val<br>                80                    85                    90 | 291 |
| gcg gag ctg gcg gcc gag cgg ggg gct cta ctg gtc ttc gcg gag cac<br>Ala Glu Leu Ala Ala Glu Arg Gly Ala Leu Leu Val Phe Ala Glu His<br>             95                    100                   105 | 339 |
| cgc tac tac ggg aag tcg ctg ccg ttc ggt gcg cag tcc acg cag cgc<br>Arg Tyr Tyr Gly Lys Ser Leu Pro Phe Gly Ala Gln Ser Thr Gln Arg<br>          110                   115                   120 | 387 |
| ggg cac acg gag ctg ctg acg gtg gag cag gcc ctg gcc gac ttc gca<br>Gly His Thr Glu Leu Leu Thr Val Glu Gln Ala Leu Ala Asp Phe Ala<br>125                    130                   135 | 435 |
| gag ctg ctc cgc gcg cta cga cgc gac ctc ggg gcc cag gat gcc ccc<br>Glu Leu Leu Arg Ala Leu Arg Arg Asp Leu Gly Ala Gln Asp Ala Pro<br>140                  145                  150               155 | 483 |
| gcc atc gcc ttc ggt gga agt tat ggg ggg atg ctc agt gcc tac ctg<br>Ala Ile Ala Phe Gly Gly Ser Tyr Gly Gly Met Leu Ser Ala Tyr Leu<br>                 160                    165                   170 | 531 |
| agg atg aag tat ccc cac ctg gtg gcg ggg gcg ctg gcg gcc agc gcg<br>Arg Met Lys Tyr Pro His Leu Val Ala Gly Ala Leu Ala Ala Ser Ala<br>             175                    180                   185 | 579 |
| ccc gtt cta gct gtg gca ggc ctc ggc gac tcc aac cag ttc ttc cgg<br>Pro Val Leu Ala Val Ala Gly Leu Gly Asp Ser Asn Gln Phe Phe Arg<br>    190                    195                    200 | 627 |
| gac gtc acg gcg gac ttt gag ggc cag agt ccc aaa tgc acc cag ggt<br>Asp Val Thr Ala Asp Phe Glu Gly Gln Ser Pro Lys Cys Thr Gln Gly<br>205                    210                   215 | 675 |
| gtg cgg gaa gcg ttc cga cag atc aag gac ttg ttc cta cag gga gcc<br>Val Arg Glu Ala Phe Arg Gln Ile Lys Asp Leu Phe Leu Gln Gly Ala<br>220                  225                  230               235 | 723 |
| tac gac acg gtc cgc tgg gag ttc ggc acc tgc cag ccg ctg tca gac<br>Tyr Asp Thr Val Arg Trp Glu Phe Gly Thr Cys Gln Pro Leu Ser Asp<br>                 240                    245                   250 | 771 |
| gag aag gac ctg acc cag ctc ttc atg ttc gcc cgg aat gcc ttc acc<br>Glu Lys Asp Leu Thr Gln Leu Phe Met Phe Ala Arg Asn Ala Phe Thr<br>             255                    260                   265 | 819 |
| gtg ctg gcc atg atg gac tac ccc tac ccc act gac ttc ctg ggt ccc<br>Val Leu Ala Met Met Asp Tyr Pro Tyr Pro Thr Asp Phe Leu Gly Pro<br>          270                   275                   280 | 867 |
| ctc cct gcc aac ccc gtc aag gtg ggc tgt gat cgg ctg ctg agt gag<br>Leu Pro Ala Asn Pro Val Lys Val Gly Cys Asp Arg Leu Leu Ser Glu<br>285                    290                   295 | 915 |

```
gcc cag agg atc acg ggg ctg cga gca ctg gca ggg ctg gtc tac aac      963
Ala Gln Arg Ile Thr Gly Leu Arg Ala Leu Ala Gly Leu Val Tyr Asn
300             305                 310                 315 gcc tcg ggc tcc gag cac tgc tac gac atc tac cgg ctc tac cac agc     1011
Ala Ser Gly Ser Glu His Cys Tyr Asp Ile Tyr Arg Leu Tyr His Ser
                320                 325                 330 tgt gct gac ccc act ggc tgc ggc acc ggc ccc gac gcc agg gcc tgg     1059
Cys Ala Asp Pro Thr Gly Cys Gly Thr Gly Pro Asp Ala Arg Ala Trp
            335                 340                 345 gac tac cag gcc tgc acc gag atc aac ctg acc ttc gcc agc aac aat     1107
Asp Tyr Gln Ala Cys Thr Glu Ile Asn Leu Thr Phe Ala Ser Asn Asn
        350                 355                 360 gtg acc gat atg ttc ccc gac ctg ccc ttc act gac gag ctc cgc cag     1155
Val Thr Asp Met Phe Pro Asp Leu Pro Phe Thr Asp Glu Leu Arg Gln
    365                 370                 375 cgg tac tgc ctg gac acc tgg ggc gtg tgg ccc cgg ccc gac tgg ctg     1203
Arg Tyr Cys Leu Asp Thr Trp Gly Val Trp Pro Arg Pro Asp Trp Leu
380                 385                 390                 395 ctg acc agc ttc tgg ggg ggt gat ctc aga gcc gcc agc aac atc atc     1251
Leu Thr Ser Phe Trp Gly Gly Asp Leu Arg Ala Ala Ser Asn Ile Ile
                400                 405                 410 ttc tcc aac ggg aac ctg gac ccc tgg gca ggg ggc ggg att cgg agg     1299
Phe Ser Asn Gly Asn Leu Asp Pro Trp Ala Gly Gly Gly Ile Arg Arg
            415                 420                 425 aac ctg agt gcc tca gtc atc gcc gtc acc atc cag ggg gga gcg cac     1347
Asn Leu Ser Ala Ser Val Ile Ala Val Thr Ile Gln Gly Gly Ala His
        430                 435                 440 cac ctc gac ctc aga gcc tcc cac cca gaa gat cct gct tcc gtg gtt     1395
His Leu Asp Leu Arg Ala Ser His Pro Glu Asp Pro Ala Ser Val Val
    445                 450                 455 gag gcg cgg aag ctg gag gcc acc atc atc ggc gag tgg gta aag gca     1443
Glu Ala Arg Lys Leu Glu Ala Thr Ile Ile Gly Glu Trp Val Lys Ala
460                 465                 470                 475 gcc agg cgt gag cag cag cca gct ctg cgt ggg ggg ccc aga ctc agc     1491
Ala Arg Arg Glu Gln Gln Pro Ala Leu Arg Gly Gly Pro Arg Leu Ser
                480                 485                 490 ctc tgagcacagg actggagggg tctcaaggct cctcatggag tggggcttc           1544
Leu actcaagcag ctggcggcag agggaagggg ctgaataaac gcctggaggc ctggcaaaaa   1604
aaaaaaaaaa aaaaaaaaaa aaaaaaaaaa aaaaaaaaaa aaaaaaaa                1653

<210> SEQ ID NO 3
<211> LENGTH: 10
<212> TYPE: PRT
<213> ORGANISM: Artificial Sequence
<220> FEATURE:
<223> OTHER INFORMATION: consensus sequence for the prolyloligopeptidase
      family from the Prosite database of protein
      patterns

<400> SEQUENCE: 3

Ile Phe Gly Gly Ser Asn Gly Gly Leu Leu
 1               5                  10

<210> SEQ ID NO 4
<211> LENGTH: 251
<212> TYPE: PRT
<213> ORGANISM: Artificial Sequence
<220> FEATURE:
<223> OTHER INFORMATION: consensus sequence for the alpha/beta hydrolase
      family from the Prosite database of protein
``` patterns

<400> SEQUENCE: 4

```
Phe Arg Val Ile Ala Leu Asp Leu Arg Gly Phe Gly Glu Ser Ser Arg
 1               5                  10                  15
Pro Ser Asp Leu Ala Asp Tyr Arg Phe Asp Asp Leu Ala Glu Asp Leu
            20                  25                  30
Glu Ala Leu Leu Asp Ala Leu Gly Leu Asp Lys Pro Val Ile Leu Val
            35                  40                  45
Gly His Ser Met Gly Gly Ala Leu Ala Ala Tyr Ala Ala Lys Tyr
        50                  55                  60
Pro Glu Glu Arg Val Lys Ala Leu Val Leu Val Ser Thr Pro Ala Pro
65                  70                  75                  80
Ala Gly Leu Ser Ser Arg Leu Phe Pro Arg Leu Gly Asn Leu Glu Gly
                85                  90                  95
Leu Leu Leu Ala Asn Phe Phe Asn Arg Leu Ser Arg Ser Val Glu Ala
                100                 105                 110
Leu Leu Gly Arg Ala Leu Lys Gln Phe Phe Leu Leu Gly Arg Pro Phe
            115                 120                 125
Val Ser Asp Phe Leu Lys Gln Ala Glu Asp Trp Leu Ser Ser Leu Ala
    130                 135                 140
Arg Pro Gly Glu Thr Asp Gly Gly Asp Gly Leu Leu Gly Tyr Ala Val
145                 150                 155                 160
Ala Leu Gly Lys Leu Leu Gln Trp Asp Arg Ser Ala Leu Lys Asp Ile
                165                 170                 175
Lys Val Pro Thr Leu Val Ile Trp Gly Asp Asp Pro Leu Val Pro
            180                 185                 190
Leu Lys Ala Ser Glu Lys Leu Ser Ala Leu Phe Pro Asn Ala Glu Val
        195                 200                 205
Val Val Ile Asp Asp Ala Gly His Leu Ala Leu Leu Glu Lys Pro Glu
    210                 215                 220
Glu Val Ala Glu Leu Ile Lys Phe Leu Ala Leu Ser Thr Asn Asx Ile
225                 230                 235                 240
Arg Asp Ala Leu Ser Thr Asn Asx Ile Arg Asp
                245                 250
```